US010288832B2

(12) United States Patent
Willis et al.

(10) Patent No.: US 10,288,832 B2
(45) Date of Patent: *May 14, 2019

(54) LIGHT BLOCKING ASSEMBLY FOR AN ANALYTE DETECTOR

(71) Applicant: FLIR Systems, Inc., Wilsonville, OR (US)

(72) Inventors: Christopher Willis, Stillwater, OK (US); Craig Aker, Stillwater, OK (US)

(73) Assignee: FLIR Systems, Inc., Wilsonville, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/588,411

(22) Filed: May 5, 2017

(65) Prior Publication Data

US 2017/0234789 A1    Aug. 17, 2017

Related U.S. Application Data

(63) Continuation of application No. 15/028,282, filed as application No. PCT/US2014/060048 on Oct. 10, 2014, now Pat. No. 9,921,385.

(60) Provisional application No. 61/889,759, filed on Oct. 11, 2013, provisional application No. 61/924,106, filed on Jan. 6, 2014.

(51) Int. Cl.
| G01N 1/10 | (2006.01) |
| G02B 7/02 | (2006.01) |
| G02B 13/14 | (2006.01) |
| H04N 5/33 | (2006.01) |
| G01N 21/03 | (2006.01) |
| H04N 5/225 | (2006.01) |

(52) U.S. Cl.
CPC .......... *G02B 7/02* (2013.01); *G01N 21/0303* (2013.01); *G02B 7/026* (2013.01); *G02B 13/14* (2013.01); *H04N 5/33* (2013.01); *H04N 5/2254* (2013.01)

(58) Field of Classification Search
CPC ... G01J 3/44; G01J 3/28; G01N 21/65; G01N 21/0303; G01N 2021/656; G02B 13/14; G02B 7/02; H04N 5/2254
USPC ................... 356/246, 301, 440; 250/339.07
See application file for complete search history.

(56) References Cited

U.S. PATENT DOCUMENTS

| 5,075,553 | A | 12/1991 | Noble et al. |
| 7,542,132 | B2* | 6/2009 | Fang ................... G01N 21/65 |
| | | | 356/301 |
| 7,799,573 | B2 | 9/2010 | Deans et al. |
| 8,245,585 | B1 | 8/2012 | Szabo et al. |
| 8,896,745 | B2* | 11/2014 | Takachi ............ H01L 27/14618 |
| | | | 348/342 |
| 9,458,451 | B2* | 10/2016 | Heinz ................ B01F 11/0045 |
| 9,921,385 | B2* | 3/2018 | Willis ..................... G02B 7/02 |

(Continued)

FOREIGN PATENT DOCUMENTS

| CN | 201489168 U | 5/2010 |
| CN | 102956653 A | 3/2013 |
| CN | 202975443 U | 6/2013 |

*Primary Examiner* — Hoa Q Pham
(74) *Attorney, Agent, or Firm* — Haynes and Boone, LLP

(57) ABSTRACT

Disclosed is an analyte detector with a light blocking assembly. The light blocking assembly includes a light blocking cartridge positioned within the bore of a sampling tip. The light blocking assembly provides fluid communication between the environment and a sensor assembly in an analyte detector while substantially precluding the passage of light.

20 Claims, 19 Drawing Sheets

(56) References Cited

U.S. PATENT DOCUMENTS

| | | | |
|---|---|---|---|
| 2004/0046121 A1* | 3/2004 | Golden | G01J 3/44 250/339.07 |
| 2012/0092543 A1 | 4/2012 | Afshari et al. | |
| 2013/0038764 A1 | 2/2013 | Takachi | |
| 2013/0208353 A1 | 8/2013 | Huddleston | |

* cited by examiner

SECTION E-E

SECTION A-A

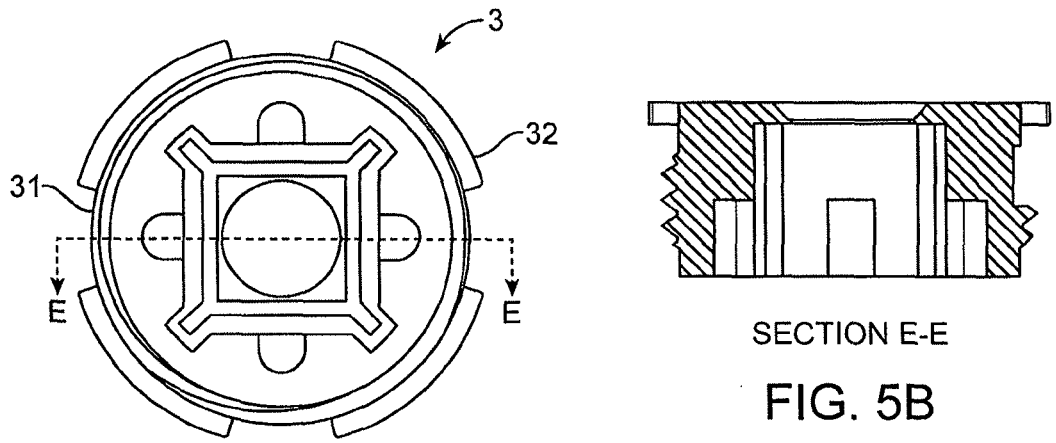
FIG. 5A
SECTION E-E
FIG. 5B
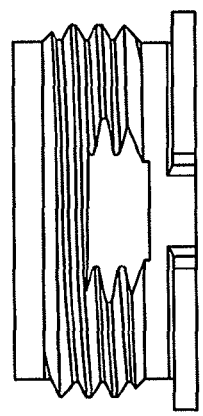
FIG. 5C
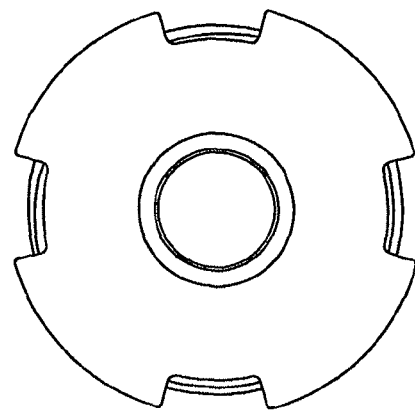
FIG. 5D
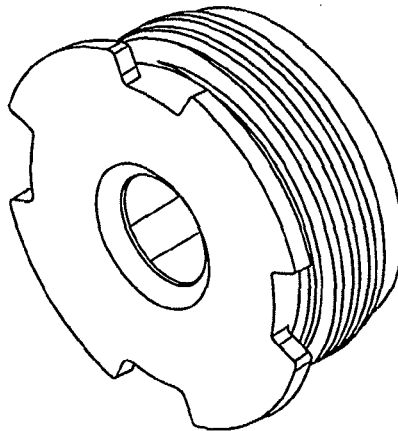
FIG. 5E

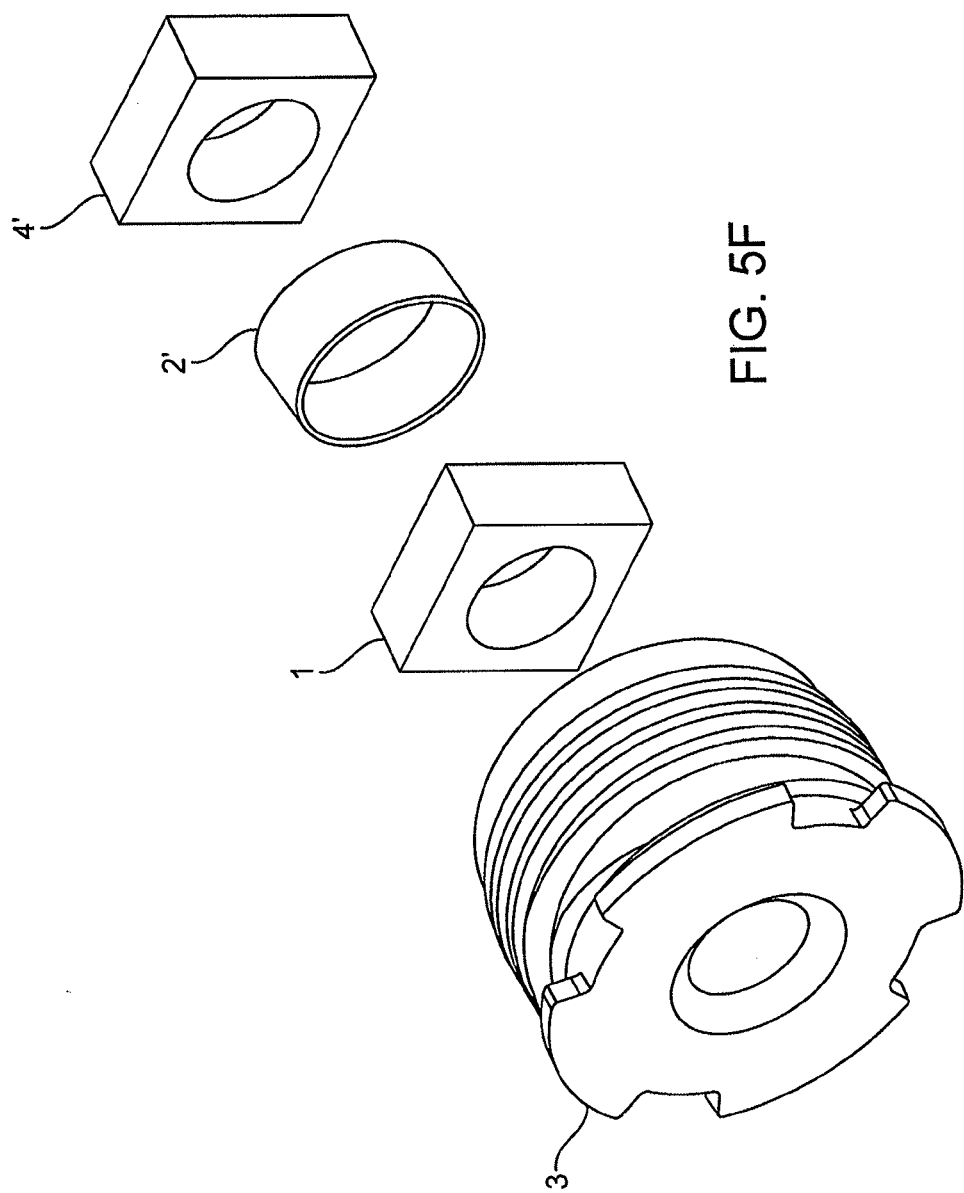

SECTION E-E

SECTION A-A

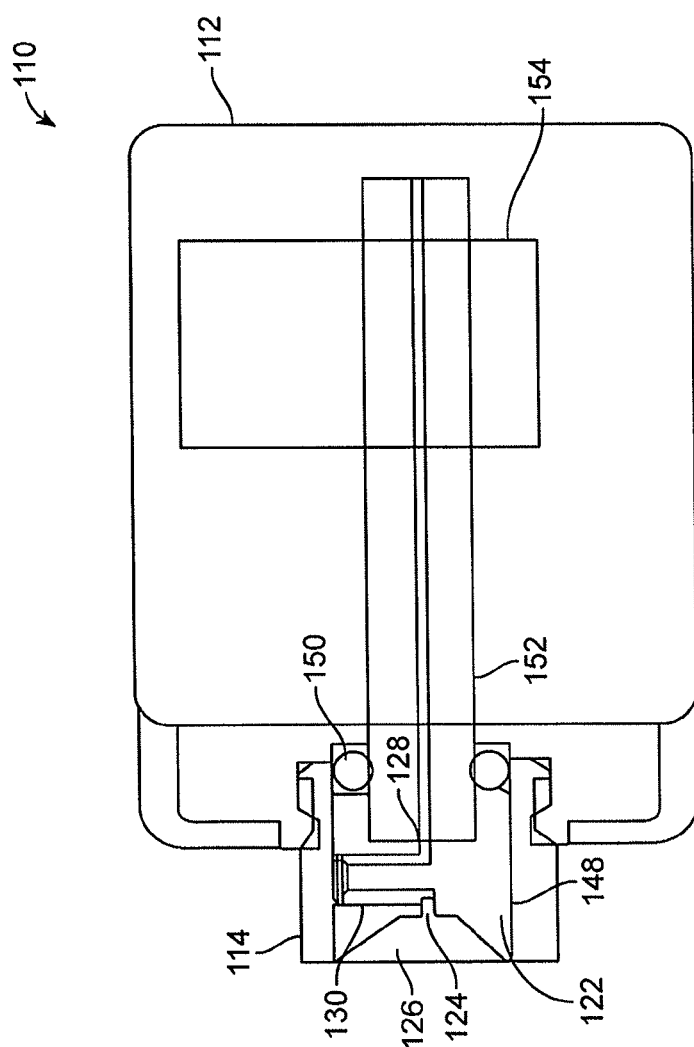

LIGHT BLOCKING ASSEMBLY FOR AN ANALYTE DETECTOR

CROSS-REFERENCE TO RELATED APPLICATIONS

The present application is a continuation of U.S. patent application Ser. No. 15/028,282, filed on Apr. 8, 2016, and entitled: "Optical Barrel Assembly, Camera Including the Same, Analyte Detector Including the Same, and Associated Methods," which was the National Stage of International Application No. PCT/US2014/060048, filed on Oct. 10, 2014, and entitled: "Optical Barrel Assembly, Camera Including the Same, Analyte Detector Including the Same, and Associated Methods," all of which are incorporated herein by reference in their entirety.

International Application No. PCT/US2014/060048 claims priority under 35 U.S.C. § 119(e) to U.S. Provisional Application No. 61/889,759, filed on Oct. 11, 2013, and entitled: "Improved Light Blocking Assembly For An Analyte Detector," and U.S. Provisional Application No. 61/924,106, filed on Jan. 6, 2014, and entitled: "Lens Barrel Assembly, Camera Including the Same, and Associated Methods," all of which are incorporated herein by reference in their entirety.

BACKGROUND OF THE INVENTION

1. Field of the Invention

Embodiments relate to a barrel assembly, a camera including the same, an analyte detector including the same, and associated methods.

2. Description of the Related Art

A system may include a barrel assembly with elements arranged therein. For example for an optical system, lenses and spacers may be aligned and assembled within a barrel to define the optical system, e.g., to define a lens barrel assembly. Typically, the barrel is cylindrical and the lenses have a circular perimeter.

SUMMARY OF THE INVENTION

One or more embodiments are directed to a lens barrel assembly, including a barrel having an inner bottom surface and an inner lateral surface extending from the inner bottom surface, the inner bottom and lateral surfaces defining a cylindrical housing, and a first optical element of a high-index material on the inner bottom surface of the barrel and surrounded by the inner lateral surface of the barrel, wherein an outer perimeter of the first optical element has a different shape than a perimeter defined by the cylindrical housing.

The first optical element may be polygonal.

The inner bottom surface of the barrel includes a polygonal pocket, the first optical element being at least partially inside the polygonal pocket.

A width of the polygonal pocket may equal a width of the polygonal first optical element, the widths of the polygonal pocket and first optical element being smaller than a width of the inner lateral surface defining the cylindrical housing.

The inner lateral surface of the cylindrical housing may surround the first optical element and is spaced apart from the optical element, the first optical element contacting only an interior of the pocket among parts of the barrel.

The lens barrel assembly may include a pocket extending from the inner bottom surface of the barrel toward an outer bottom surface of the barrel, a depth of the pocket being smaller than a distance between the inner and outer bottom surfaces of the barrel.

The pocket may have a polygonal shape.

A width of the pocket may be smaller than a width of the inner surface of the cylindrical housing.

The first optical element may be at least partially inserted into the pocket.

The first optical element may be in direct contact with a bottom and a sidewall of the pocket.

The lens barrel assembly may include a second optical element of a high-index material on the first optical element and inside the cylindrical housing.

The lens barrel assembly may include a spacer between the first and second optical elements.

The lens barrel assembly may include a first polygonal pocket in a surface of the barrel facing the first optical element, the first optical element being at least partially inserted in the first polygonal pocket of the barrel, and a second polygonal pocket in a surface of the spacer facing the second optical element, the second optical element having a polygonal outer perimeter and being at least partially inserted in the second polygonal pocket of the spacer.

The spacer may include a pocket, the second optical element may have an outer perimeter with a different shape than an outer perimeter of the spacer, and the second optical element being at least inside the pocket of the spacer.

The inner bottom surface of the barrel may include a pocket, the first optical element being at least partially inside the pocket of the barrel.

The first and second optical elements may have polygonal perimeters having sizes and shapes corresponding to respective pockets of the barrel and the spacer.

The inner lateral surface of the cylindrical housing surrounds each of the first and second optical elements and is spaced apart from each of the first and second optical elements, the first and second optical elements contacting only an interior of their respective pockets.

The spacer may have a circular outer perimeter with an aperture extending through the spacer, a polygonal pocket extending from an inner surface of the spacer toward an outer surface of the spacer and surrounding the aperture. The second optical element may have a polygonal outer perimeter corresponding to the polygonal pocket, the second optical element overlapping the aperture.

An inner diameter of the spacer may have a non-uniform width. The non-uniform width of the inner diameter of the spacer may be configured to minimize stray light.

The inner diameter of the spacer may include first through fourth portions, a first portion defining a polygonal pocket in the spacer and accommodating the second optical element, a second portion having a smaller width than the first portion, a third portion having a curved surface, and a fourth portion having an inclined surface.

The spacer may include a stepped-portion in an outer surface of the spacer, the second optical element being on an inner surface of the spacer.

The stepped-portion may only be in a periphery of the outer surface of the spacer, a central portion of the spacer extends above the stepped-portion.

The spacer may include protrusions between an outer diameter of the spacer and an inner diameter of the cylindrical housing, the protrusions defining a space between the outer diameter of the spacer and the inner diameter of the cylindrical housing.

The protrusions may be spaced apart from each other along the outer diameter of the spacer, the space between the outer diameter of the spacer and the inner diameter of the cylindrical housing being further defined by every two adjacent protrusions.

The spacer may include notches in bottom surfaces of the protrusions, an inner space of the spacer defined by an inner diameter of the spacer being in fluid communication with the space between the spacer and the cylindrical housing through the notches.

The inner bottom surface of the barrel may further include a corner relief.

The corner relief may extend to a predetermined depth from the inner bottom surface of the barrel toward and outer surface of the barrel, the corner relief being aligned with a corner of the first optical element.

The inner bottom surface of the barrel may include an edge relief extending along an edge of the first optical element.

The edge relief may define a gap between a surface of the barrel and a surface of the first optical element.

The spacer may have a circular outer perimeter with an aperture extending through the spacer, the first and second optical elements being flush with the spacer.

The lens barrel assembly may include a pocket inside the barrel, the pocket having an outer perimeter that corresponds to the outer perimeter of the first optical element, the first optical element being at least partially inside the pocket.

The pocket may be integral with the inner lateral surface of the barrel.

The pocket may be integral with the inner bottom surface of the barrel.

The pocket may be in a separate element inserted in the barrel.

The separate element may have a circular outer perimeter.

The pocket may include corner reliefs.

The corner reliefs may include passages extending from corners of the pocket.

The pocket may include edge reliefs extending along a periphery of the pocket between the corner reliefs.

The edge reliefs may be passages further from the inner bottom surface of the barrel than the first optical element.

The pocket may include edge reliefs extending along a periphery of the pocket.

The edge reliefs may be passages further from the inner bottom surface of the barrel than the first optical element.

Each edge relief may define a gap between a surface of the pocket and a surface of the first optical element.

One or more embodiments is directed to a lens barrel assembly including a barrel having a circular base and a cylindrical structure on the circular base, the circular base and cylindrical structure defining a housing, and the circular base including a recess to a predetermined depth, an aperture through the circular base of the barrel, the recess surrounding the aperture, and a first optical element of a high-index material at least partially inside the recess of the circular base, the first optical element having a polygonal shape.

The lens barrel assembly may include a second optical element on the first optical element and inside the housing, the second optical element having a polygonal shape.

The lens barrel assembly may include a spacer between the first and second optical elements.

One or more embodiments is directed to a lens barrel assembly including a barrel structure having a circular inner perimeter, the inner perimeter surrounding a recess, and a first optical element of a high-index material inside the barrel structure, an outer perimeter of the first optical element being surrounded by a sidewall of the recess, the first optical element having a non-circular outer perimeter.

The lens barrel assembly may include a second optical element on the first optical element and inside the barrel structure.

The lens barrel assembly may include a spacer, separate from the barrel, between the first and second optical elements.

One or more embodiments is directed to a barrel for an optical system, the barrel including a cylindrical structure on a circular base, the cylindrical structure and circular base defining a housing, a recess to a predetermined depth in the circular base, a perimeter of the recess being non-circular, and an aperture through the circular base, the recess surrounding and overlapping the aperture.

One or more embodiments is directed to a spacer for a barrel assembly, the spacer including a base structure with a circular outer perimeter, the outer perimeter of the base structure facing an inner perimeter of the barrel assembly, an aperture through an entire thickness of the base structure, and a non-circular recess to a predetermined depth in the base structure, the recess surrounding the aperture and only partially extending through the base structure.

One or more embodiments is directed to a camera including a sensor, and a lens barrel assembly through which light is incident on the sensor, the lens barrel assembly including a barrel structure having a circular inner perimeter, the inner perimeter surrounding a recess, and a first optical element of a high-index material inside the barrel structure, an outer perimeter of the first optical element being surrounded by a sidewall of the recess and having a non-circular outer perimeter.

The camera may include a second optical element inside the barrel structure.

The camera may include a spacer between the first and second optical elements.

One or more embodiments is directed to a method of assembling a lens barrel, including singulating a first optical element die of a high-index material from a wafer of a plurality of first optical elements, the first optical element die having a non-circular profile, providing a barrel having an inner bottom surface and an inner lateral surface extending from the inner bottom surface, the inner bottom and lateral surfaces defining a cylindrical housing, and providing the first optical element die inside the cylindrical housing and surrounded by the inner lateral surface of the barrel.

The method may include providing a second optical element of a high-index material inside the cylindrical housing and surrounded by the inner lateral surface of the barrel.

The method may include providing a spacer between the first and second optical element dies.

The second optical element may be a second optical element die singulated from a wafer having a plurality of second optical elements, the second optical element die having a non-circular profile.

The second optical element die may be larger than the first optical element die.

An orientation of the second optical element die may be rotated by 45° relative to an orientation of the first optical element die.

A surface of the spacer facing the second optical element die may have a recessed portion corresponding to the non-circular profile of the second optical element die and the second optical element die is on the surface of the spacer facing the second optical element die.

The inner bottom surface of the barrel may have a recessed portion corresponding to the non-circular profile of the first optical element die and the first optical element die is on the inner bottom surface of the barrel.

The recessed portion of the inner bottom surface of the barrel and the recessed portion of the spacer may include corner reliefs.

The method may include forming a pocket inside the barrel, the pocket having an outer perimeter that corresponds to the outer perimeter of the first optical element, the first optical element being at least partially inside the pocket.

The pocket may be integral with the inner lateral surface of the barrel, integral with the inner bottom surface of the barrel, or in a separate element inserted in the barrel. The separate element may have a circular outer perimeter.

The pocket may include corner reliefs and/or edge reliefs. The corner reliefs may include passages extending from corners of the pocket. The edge reliefs may extend along a periphery of the pocket, e.g., between corner reliefs. The edge reliefs may be passages further from the inner bottom surface of the barrel than the first optical element.

One or more embodiments is directed to a lens barrel assembly, including a barrel having an inner bottom surface and an inner lateral surface extending from the inner bottom surface, the inner bottom and lateral surfaces defining a cylindrical housing, a first optical element on the inner bottom surface of the barrel and surrounded by the inner lateral surface of the barrel, and a second optical element on the first optical element and inside the cylindrical housing, wherein an outer perimeter of at least one of the first and second optical elements having a different shape than a perimeter defined by the cylindrical housing.

The first optical element may be polygonal.

The inner bottom surface of the barrel may include a polygonal pocket, the first optical element being at least partially inside the polygonal pocket.

A width of the polygonal pocket may equal a width of the polygonal first optical element, the widths of the polygonal pocket and first optical element being smaller than a width of the inner lateral surface defining the cylindrical housing.

The inner lateral surface of the cylindrical housing may surround the first optical element and may be spaced apart from the optical element, the first optical element contacting only an interior of the pocket among parts of the barrel.

The lens barrel assembly may include a pocket extending from the inner bottom surface of the barrel toward an outer bottom surface of the barrel, a depth of the pocket being smaller than a distance between the inner and outer bottom surfaces of the barrel.

The pocket may have a polygonal shape. A width of the pocket may be smaller than a width of the inner surface of the cylindrical housing. The first optical element may be at least partially inserted into the pocket. The first optical element may be in direct contact with a bottom and a sidewall of the pocket.

The lens barrel assembly may include a spacer between the first and second optical elements.

The lens barrel assembly may include a first polygonal pocket in a surface of the barrel facing the first optical element, the first optical element being at least partially inserted in the first polygonal pocket of the barrel, and a second polygonal pocket in a surface of the spacer facing the second optical element, the second optical element having a polygonal outer perimeter and being at least partially inserted in the second polygonal pocket of the spacer.

The spacer may include a pocket, the second optical element having an outer perimeter with a different shape than an outer perimeter of the spacer, and the second optical element being at least inside the pocket of the spacer. The inner bottom surface of the barrel may include a pocket, the first optical element being at least partially inside the pocket of the barrel. The first and second optical elements may have polygonal perimeters having sizes and shapes corresponding to respective pockets of the barrel and the spacer.

The inner lateral surface of the cylindrical housing may surround each of the first and second optical elements and may be spaced apart from each of the first and second optical elements, the first and second optical elements contacting only an interior of their respective pockets.

The spacer may have a circular outer perimeter with an aperture extending through the spacer, a polygonal pocket extending from an inner surface of the spacer toward an outer surface of the spacer and surrounding the aperture, and the second optical element may have a polygonal outer perimeter corresponding to the polygonal pocket, the second optical element overlapping the aperture.

An inner diameter of the spacer may have a non-uniform width. The non-uniform width of the inner diameter of the spacer may be configured to minimize stray light. The inner diameter of the spacer includes first through fourth portions, a first portion defining a polygonal pocket in the spacer and accommodating the second optical element, a second portion having a smaller width than the first portion, a third portion having a curved surface, and a fourth portion having an inclined surface.

The spacer may include a stepped-portion in an outer surface of the spacer, the second optical element being on an inner surface of the spacer. The stepped-portion may be only in a periphery of the outer surface of the spacer, a central portion of the spacer extends above the stepped-portion.

The spacer may include protrusions between an outer diameter of the spacer and an inner diameter of the cylindrical housing, the protrusions defining a space between the outer diameter of the spacer and the inner diameter of the cylindrical housing. The protrusions may be spaced apart from each other along the outer diameter of the spacer, the space between the outer diameter of the spacer and the inner diameter of the cylindrical housing being further defined by every two adjacent protrusions.

The spacer may include notches in bottom surfaces of the protrusions, an inner space of the spacer defined by an inner diameter of the spacer being in fluid communication with the space between the spacer and the cylindrical housing through the notches.

The inner bottom surface of the barrel may include a corner relief and/or an edge relief. The corner relief may extend to a predetermined depth from the inner bottom surface of the barrel toward and outer surface of the barrel, the corner relief being aligned with a corner of the first optical element. The edge relief may extend along an edge of the first optical element. The edge relief may define a gap between a surface of the barrel and a surface of the first optical element.

The spacer may have a circular outer perimeter with an aperture extending through the spacer, the first and second optical elements being flush with the spacer.

The lens barrel assembly may include a pocket inside the barrel, the pocket having an outer perimeter that corresponds to the outer perimeter of the first optical element, the first optical element being at least partially inside the pocket.

The pocket may be integral with the inner lateral surface of the barrel, integral with the inner bottom surface of the barrel, or be in a separate element inserted in the barrel. The separate element may have a circular outer perimeter.

The pocket may include corner reliefs and/or edge reliefs. The corner reliefs include passages extending from corners of the pocket. The edge reliefs may extend along a periphery of the pocket, e.g., between the corner reliefs. The edge reliefs may be passages further from the inner bottom surface of the barrel than the first optical element. Each edge relief may define a gap between a surface of the pocket and a surface of the first optical element.

One or more embodiments is directed to a lens barrel assembly, including a barrel having a circular base and a cylindrical structure on the circular base, the circular base and cylindrical structure defining a housing, and the circular base including a recess to a predetermined depth, an aperture through the circular base of the barrel, the recess surrounding the aperture, a first optical element inside the barrel structure, an outer perimeter of the first optical element being surrounded by a sidewall of the recess, and a second optical element on the first optical element and inside the barrel, at least one of the first and second optical elements having a non-circular outer perimeter.

The lens barrel assembly may include a spacer between the first and second optical elements.

One or more embodiments is directed to a lens barrel assembly, including a barrel structure having a circular inner perimeter, the inner perimeter surrounding a recess, a first optical element inside the barrel structure, an outer perimeter of the first optical element being surrounded by a sidewall of the recess, and a second optical element on the first optical element and inside the barrel structure, at least one of the first and second optical elements having a non-circular outer perimeter.

The lens barrel assembly may include a spacer, separate from the barrel, between the first and second optical elements.

One or more embodiments is directed to a camera, including a sensor; and a lens barrel assembly through which light is incident on the sensor, the lens barrel assembly including a barrel structure having a circular inner perimeter, the inner perimeter surrounding a recess, a first optical element inside the barrel structure, an outer perimeter of the first optical element being surrounded by a sidewall of the recess, and a second optical element on the first optical element and inside the barrel structure, at least one of the first and second optical elements having a non-circular outer perimeter.

The camera may include a spacer between the first and second optical elements.

One or more embodiments is directed to a method of assembling a lens barrel, including singulating a first optical element die from a wafer of a plurality of first optical elements, providing a barrel having an inner bottom surface and an inner lateral surface extending from the inner bottom surface, the inner bottom and lateral surfaces defining a cylindrical housing, and providing the first optical element die and a second optical element inside the cylindrical housing and surrounded by the inner lateral surface of the barrel.

The method may include providing a spacer between the first and second optical element dies.

The second optical element maybe a second optical element die singulated from a wafer having a plurality of second optical elements, the second optical element die having a non-circular profile.

The second optical element die may be larger than the first optical element die.

An orientation of the second optical element die is rotated, e.g., by 45°, relative to an orientation of the first optical element die.

A surface of the spacer facing the second optical element die may have a recessed portion corresponding to the non-circular profile of the second optical element die and the second optical element die is on the surface of the spacer facing the second optical element die.

The inner bottom surface of the barrel has a recessed portion corresponding to a non-circular profile of the first optical element die and the first optical element die is on the inner bottom surface of the barrel.

The recessed portion of the inner bottom surface of the barrel and the recessed portion of the spacer may include corner reliefs.

The method may include forming a pocket inside the barrel, the pocket having an outer perimeter that corresponds to the outer perimeter of the first optical element, the first optical element being at least partially inside the pocket. The method pocket may be integral with the inner lateral surface of the barrel, the inner bottom surface of the barrel, or may be in a separate element inserted in the barrel. The separate element may have a circular outer perimeter.

The pocket may include corner reliefs and/or edge reliefs. The corner reliefs may include passages extending from corners of the pocket. The edge reliefs extending may be along a periphery of the pocket, e.g., between the corner reliefs. The edge reliefs may be passages further from the inner bottom surface of the barrel than the first optical element. The edge reliefs may be passages further from the inner bottom surface of the barrel than the first optical element.

One or more embodiments is directed to an analyte detector including a housing, a sensor assembly positioned within the housing, a sampling tip positioned carried by the housing, the sampling tip having a first end and a second end and a bore passing through the sampling tip, a light blocking cartridge within the bore of the sampling tip, the light blocking cartridge having an inlet port and an outlet port in fluid communication with one another wherein the fluid path between the inlet port and the outlet port has at least two angular transitions and wherein a portion of the fluid path is defined by the inner wall of the sampling tip and wherein the light blocking cartridge provides fluid communication between the exterior of the housing and the sensor assembly, sealing material positioned to obscure the mating interface between the sampling tip and the light blocking cartridge.

One or more embodiments is directed to an analyte detector including a housing, a sampling tip positioned carried by the housing, the sampling tip having a first end and a second end and a bore passing through the sampling tip, a light blocking cartridge positioned within the bore of the sampling tip, wherein the light blocking cartridge has a recessed sample collection area in a first end wall, an inlet port positioned within the sample collect area and an outlet port located on the second end wall of the light blocking cartridge, the outlet port and inlet port in fluid communication, the fluid path connecting the inlet and outlet ports having at least two angular transitions in the fluid path, and wherein at least a portion of the fluid path is defined by the inner surface of the sampling tip, sealing material positioned to obscure the mating interface between the sampling tip and the light blocking cartridge.

One or more embodiments is directed to an analyte detector including a housing, a sampling tip positioned carried by the housing, the sampling tip having a first end and a second end, a bore passing through the sampling tip and an inwardly projecting flange carried by the second end, a light blocking cartridge positioned within the bore of the sampling tip, wherein the light blocking cartridge has a recessed sample collection area in a first end wall, an inlet port positioned within the sample collect area and an outlet port located on the second end wall of the light blocking cartridge, the outlet port and inlet port in fluid communication, the fluid path connecting the inlet and outlet ports having at least two angular transitions in the fluid path, and wherein at least a portion of the fluid path is defined by the inner surface of the sampling tip, the light blocking cartridge positioned within the bore of the sampling tip such that second end of the light blocking cartridge contacts the inwardly projecting flange of the sampling tip.

The light blocking cartridge may be press fitted within said bore of said sampling tip.

The angular change in the fluid path may be between about 10° and about 170°.

The angular change in the fluid path may be between about 20° and about 120°.

The angular change in the fluid path may be between about 80° and about 110°.

The sealing material may be one of room temperature vulcanizing (RTV) sealant, polyurethane, hydrogenated nitrile butadiene rubber (HNBR), ethylene propylene diene monomer (EPDM), silicone, fluoro-elastomer rubber, neoprene and polytetrafluoroethylene (PTFE)

The sealing material may be positioned on the second end of the sampling tip.

The analyte detector may include a port positioned to receive collected analyte exiting from the outlet port.

The sealing material may engage the outer surface of the port.

The bore of the sampling tip may be greater in diameter than the inner bore of the detector port.

The light blocking assembly may be between the environment and the sensor assembly.

One or more embodiments is directed to an optical barrel assembly, including a barrel having an inner bottom surface and an inner lateral surface extending from the inner bottom surface, the inner bottom and lateral surfaces defining a cylindrical housing, and a first element surrounded by the inner lateral surface of the barrel, wherein an outer perimeter of the first element has a different shape than a perimeter defined by the cylindrical housing.

The first element may be a first optical element of a high-index material.

The first optical element may be polygonal.

The inner bottom surface of the barrel may include a polygonal pocket, the first optical element being at least partially inside the polygonal pocket.

A width of the polygonal pocket may equal a width of the polygonal first optical element, the widths of the polygonal pocket and first optical element being smaller than a width of the inner lateral surface defining the cylindrical housing.

The optical barrel assembly may include a second optical element of a high-index material on the first optical element and inside the cylindrical housing.

The optical barrel assembly may include a spacer between the first and second optical elements.

An inner diameter of the spacer may have a non-uniform width.

The non-uniform width of the inner diameter of the spacer may be configured to minimize stray light.

The barrel may be a bore of a sampling tip and the first element is a light blocking cartridge having an inlet port and an outlet port in fluid communication with one another wherein a fluid path between the inlet port and the outlet port has at least two angular transitions and wherein a portion of the fluid path is defined by an inner wall of the bore of the sampling tip and wherein the light blocking cartridge provides fluid communication between the exterior of the barrel and a sensor assembly.

The optical barrel assembly may include sealing material between the light blocking cartridge and the bore adjacent the outlet port.

The sampling tip may include an inwardly projecting flange adjacent the outlet port, the light blocking cartridge contacting the inwardly projecting flange.

The lateral surface may include an inwardly projecting structure in contact with the element.

The inwardly projecting structure may be in integral with the barrel.

The optical barrel assembly may include a pocket matching the outer perimeter of the first element, the first element being at least partially inside the pocket.

The pocket may be integral with the barrel.

One or more embodiments is directed to a detector, including a sensor, and an optical barrel assembly including a barrel having an inner bottom surface and an inner lateral surface extending from the inner bottom surface, the inner bottom and lateral surfaces defining a cylindrical housing, and a first element surrounded by the inner lateral surface of the barrel, wherein an outer perimeter of the first element has a different shape than a perimeter defined by the cylindrical housing.

The sensor may be a long wavelength infrared (LWIR) sensor.

The first element may be an optical element of a high-index material.

The sensor may be a light sensor.

The barrel may be a bore of a sampling tip and the first element is a light blocking cartridge having an inlet port and an outlet port in fluid communication with one another wherein the fluid path between the inlet port and the outlet port has at least two angular transitions and wherein a portion of the fluid path is defined by an inner wall of the sampling tip and wherein the light blocking cartridge provides fluid communication between the exterior of the barrel and a sensor assembly.

BRIEF DESCRIPTION OF THE DRAWINGS

Features and advantages will become apparent to those of skill in the art by describing in detail exemplary embodiments with reference to the attached drawings, in which:

FIG. 5A illustrates a bottom, plan view of a lens barrel according to another embodiment;

FIG. 5B illustrates a cross-sectional view along line E-E in FIG. 5A;

FIG. 5C illustrates a side view of the lens barrel in FIG. 5A;

FIG. 5D illustrates a plan view of a front of the lens barrel in FIG. 5A;

FIG. 5E illustrates a perspective view of the lens barrel in FIG. 5A;

FIG. 5F illustrates an exploded perspective view of the lens barrel in FIG. 5A;

FIG. 13 illustrates a side cut-away view of an analyte detector with a sampling tip according to an embodiment installed;

DETAILED DESCRIPTION

Figure 1A:
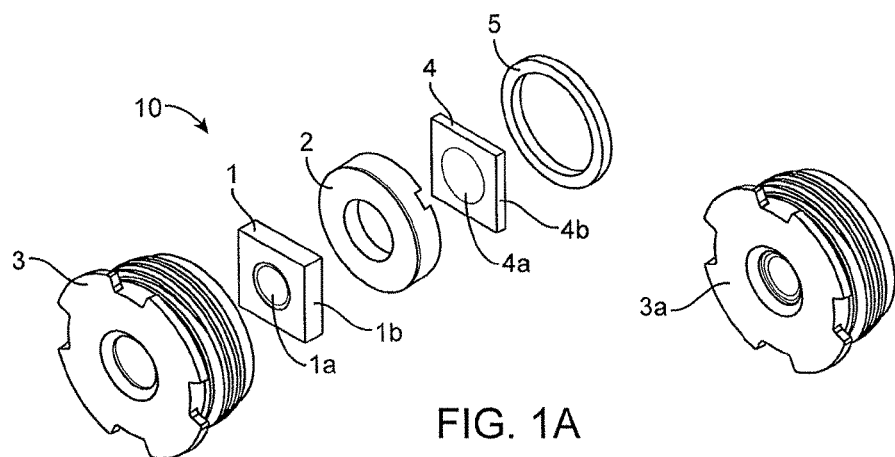
FIG. 1A illustrates assembled and exploded perspective views of a lens barrel according to an embodiment, as viewed from a front of the lens barrel.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete.

In designing long wavelength infrared (LWIR) sensors, also known as thermal imagers, materials for use as thermal lenses typically have high transmission in the LWIR waveband of 7.5-13.5 µm. Current typical materials for thermal lenses include germanium (Ge), chalcogenide glass, zinc selenide (ZnSe), and zinc sulfide (ZnS). However, many optical materials having other desirable properties are excluded due to absorption in the LWIR waveband of 7.5-13.5 µm.

As described in detail below in commonly owned, pending U.S. patent application Ser. No. 13/835,188, which is hereby incorporated by reference in its entirety, as designs for LWIR sensors shrink, e.g., for use in mobile devices, a thickness of material used for thermal lenses may decrease sufficiently to allow materials that are typically considered too absorptive in the LWIR waveband to be used as thermal lenses. This allows the use of other materials, e.g., silicon, that have an absorption band in the LWIR waveband, but offer other advantages, e.g., ease of wafer level manufacturability, low coefficient of thermal expansion, low dispersion, etc., to be employed.

The optical elements discussed in detail below may be operational over any subset of the LWIR waveband. These optical elements are designed to be made in a high index material, i.e., greater than 1.8, e.g., greater than 2.2, having an absorption per mm of thickness less than 75% in the operational waveband, and an absorption per mm of thickness greater than 75% in a visible waveband of 400-650 nm. While silicon meets these parameters and provides advantages noted above, other materials that meet these parameters may also be used.

Since traditional optics have round outer diameters, barrels have round, e.g., circular, inner diameters. In contrast, wafer-level optics having circular shapes are much more difficult to manufacture than those having polygonal shapes. However, while polygonal optics may be secured on a wafer level before being singulated, in some systems, e.g., a camera, a barrel assembly may be desirable. However, alignment of wafer-level polygonal-shaped optics into the round barrel assemblies may not be practical.

Therefore, according to embodiments, barrels, e.g., for use in cameras, are manufactured, e.g., injection molded or machined, with polygonal, e.g., square, hexagonal, etc., alignment features for aligning various wafer-level polygonal-shaped optics, rather than round-shaped optics, into the barrel assembly. That is, polygonal, e.g., square, hexagonal, etc., pockets are formed inside the barrel, e.g., in an inner surface of the barrel and/or in a spacer positioned in the barrel, so an inner diameter of the barrel includes the polygonal pockets. Accordingly, wafer-level, polygonal-shaped optics, i.e., polygonal die lenses, can be aligned and integrated in the barrel, e.g., fit into the barrel by using the polygonal pockets, thereby providing passive alignment between the barrel and the wafer-level, polygonal-shaped optics to form a barrel assembly.

Figure 1B:
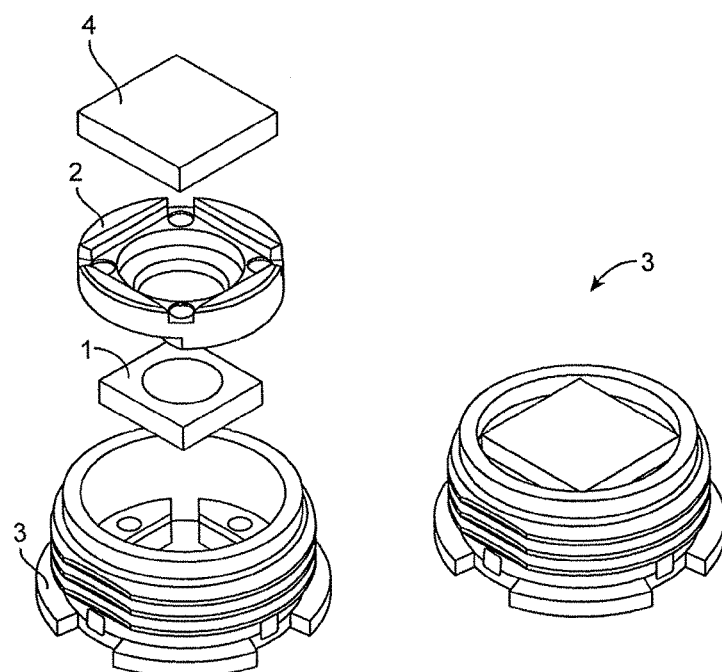
FIG. 1B illustrates assembled and exploded perspective views of the lens barrel in FIG. 1A, as viewed from a back of the lens barrel.

In detail, referring to FIGS. 1A and 1B, a barrel assembly 10 may include a first optical element 1, a second optical element 4, a spacer 2 between the optical elements, and a retaining ring 5 inside a barrel 3. The barrel 3 and the spacer 2 may be shaped to have circular outer profiles, e.g., circular diameters, while the first and second optical elements 1 and 4 are shaped to have polygonal, e.g., square, hexagonal, etc., outer profiles, e.g., polygonal outer perimeters 1b, 4b with a circular lens 1a, 4a on at least one surface thereof. The spacer 2 may provide separation between the first and second optical elements 1 and 4.

Figure 2A:
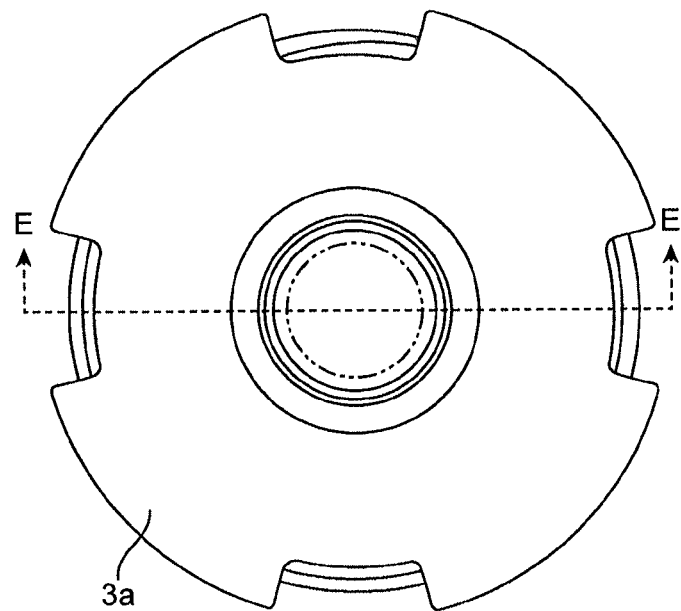
FIG. 2A illustrates a schematic plan view of a front of the lens barrel in FIG. 1A.
Figure 2B:
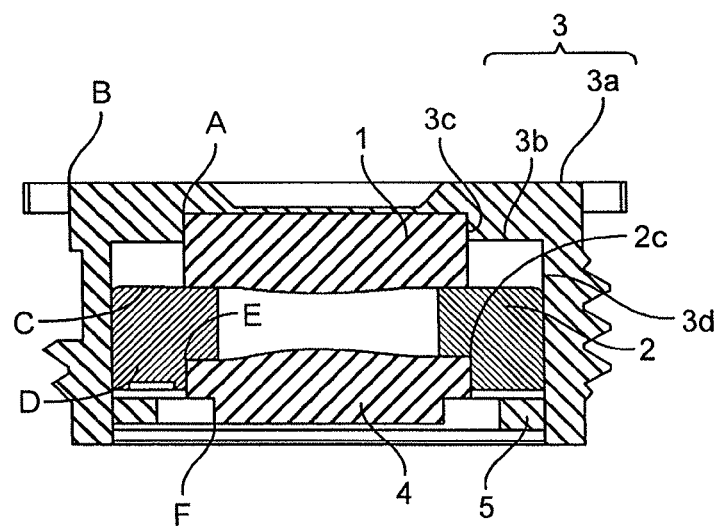
FIG. 2B illustrates a cross-sectional view along line E-E in FIG. 2A.

Referring to FIGS. 2A and 2B, according to embodiments, the barrel 3 and the spacer 2 include polygonal pockets in respective inner diameters to accommodate the polygonal shape of the first and second optical elements 1 and 4, respectively. As such, the polygonal optical elements 1 and 4 are aligned, e.g., fit, inside the barrel 3 and/or the spacer 2 despite the round, i.e., circular, shape.

In detail, as illustrated in FIG. 2B, the barrel 3 defines a housing for a plurality of elements. The barrel 3 may be a threaded barrel (FIG. 1B and FIG. 3C), such that a distance between a lens system housed therein and a sensor, i.e., along the z-axis, may be altered. As illustrated therein, the lens system may include the first optical element 1 and the second optical element 4 separated by the spacer 2 providing an air gap between surfaces B and E. A surface A of the first optical element 1 is an input surface of the lens system, and a surface F of the second optical element 4 is a final surface of the lens system. At least one of surface A and B, and at least one of surfaces E and F has optical power, e.g., is curved. One or all of the powered surfaces may be aspheric. The surfaces B and E may include relative planar portions, i.e., flat regions, in a periphery thereof to facilitate securing of the spacer 2 thereto.

The lens system may also include an aperture stop. For example, the aperture stop may be adjacent surface A, e.g., directly on surface A, of the first optical element 1. The aperture stop may be made of metal, e.g., chromium, a dyed polymer, or any suitable material. The aperture stop may be at any appropriate location within the lens system.

Figure 3A:
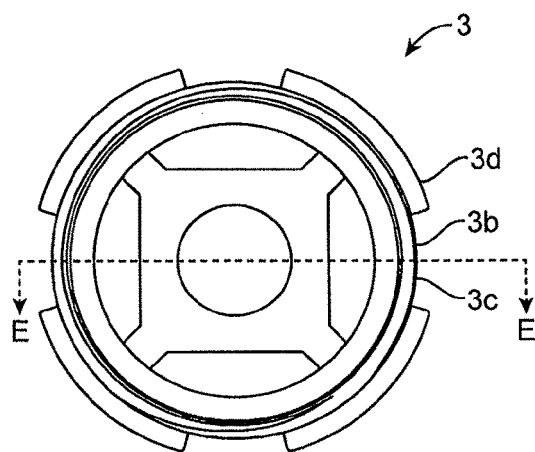
FIG. 3A illustrates a bottom plan view of the lens barrel in FIG. 1A.
Figure 10A:
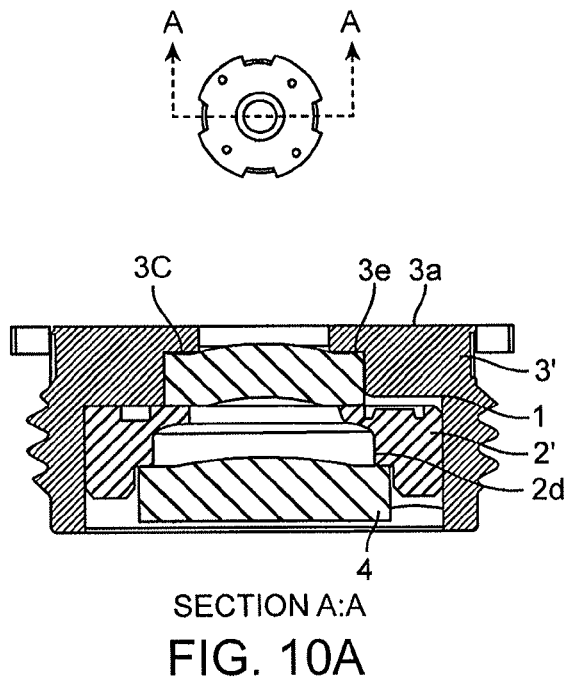
FIG. 10A illustrates a cross-sectional view of a lens barrel according to another embodiment.

As illustrated in FIG. 2B, the barrel 3 includes an outer surface 3a facing an exterior of the barrel 3, and an inner surface 3b opposite and parallel to the outer surface 3a and facing an interior of the barrel 3. The barrel 3 may include an aperture extending between the inner and outer surfaces 3a and 3b (FIG. 3A and FIG. 3D). The inner surface 3b of the barrel 3 includes a recess defining a polygonal pocket 3c, as will be discussed in detail with reference to FIGS. 3A-3B. As further illustrated in FIG. 2B, the first optical element 1 is inserted into and is aligned with, e.g., fits into, the polygonal pocket 3c, and the spacer 2 and the second optical element 4 are stacked on the first optical element 1. Further, the spacer 2 may include a recess defining a polygonal pocket 2c, as will be discussed in detail with reference to FIGS. 4C-4D, so the second optical element 4 is inserted into and aligned with, e.g., fits into, the polygonal pocket 2c of the spacer 2. Therefore, the spacer 2 is used for registration, e.g., securing and/or alignment of the optical elements, as well as separation between the optical elements. Referring to FIGS. 1B and 10A, epoxy may be dispensed around edges of the second optical element 4 and the spacer 2 for support, e.g., after the second optical element 4 is inserted into the spacer 2 in FIG. 1B.

Figure 3B:
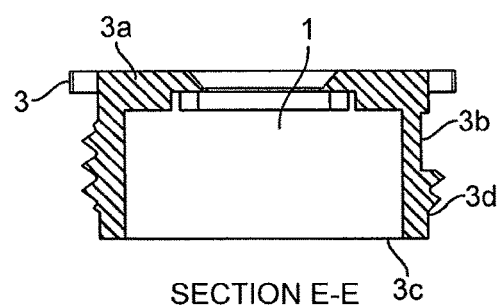
FIG. 3B illustrates a cross-sectional view along line E-E in FIG. 3A.
Figure 3C:
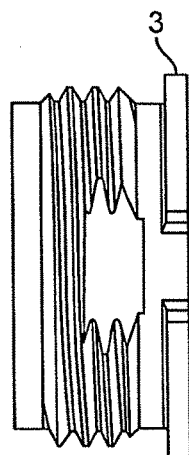
FIG. 3C illustrates a side view of the lens barrel in FIG. 1A.
Figure 3D:
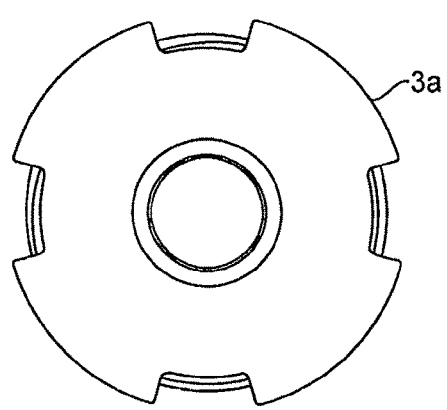
FIG. 3D illustrates a plan view of a front of the lens barrel in FIG. 1A.

In detail, as illustrated in FIGS. 3A-3B, the inner surface 3b of the barrel 3 may have a stepped-structure, e.g., a flat surface and a recess extending from the flat surface toward the outer surface 3a, to include the polygonal pocket 3c, so a polygonal structure may be accommodated in the polygonal pocket 3c. The polygonal pocket 3c overlaps the aperture of the barrel 3. For example, when viewed from a planar view (FIG. 3A), the polygonal pocket 3c may be a polygonal recess having a depth extending from the inner surface 3b of the barrel 3 toward the outer surface 3a of the barrel 3. For example, referring to FIG. 3B, if a distance along the z-axis between the inner and outer surfaces 3b and 3a of the barrel 3 is a predetermined distance, e.g., about 0.6 mm, a depth of the polygonal pocket 3c may be about half the predetermined distance, e.g., about 0.30, as measured from the inner surface 3b to the bottom of the polygonal pocket 3c.

The polygonal pocket 3c may correspond in size and shape to the first optical element 1, so at least a portion of the first optical element 1 may be aligned to fit inside the polygonal pocket 3c. For example, as illustrated in FIG. 3B, a thickness of the first optical element 1 may equal the depth of the polygonal pocket 3c, so the entire first optical element 1, e.g., in terms of depth and width, may fit inside the polygonal pocket 3c.

For example, when viewed from a planar view (FIG. 3A), the polygonal pocket 3c may have a polygonal cross-section, e.g., a square cross-section having a side length of about 2.5 mm. For example, the polygonal pocket 3c may further extend from each corner of the square cross-section, e.g., having a width of about 0.50 mm, so two of these extensions, i.e., corner cut-outs, may be aligned on a diagonal of the square cross-section. These extensions allow corners of the first optical element 1 to be spaced apart from a surface of the barrel 3 in the xy-plane and allow the first optical element 1 to be flush with the mounting surface in the z-axis, e.g., allow the first optical element 1 to sit all the way on the mounting surface.

As illustrated in FIGS. 3A-3B, the polygonal pocket 3c is surrounded, e.g., completely surrounded, by an inner perimeter 3d of the barrel 3. For example, the polygonal pocket 3c may be concentric with respect to the inner perimeter 3d of the barrel 3, and may have a smaller width, e.g., a smaller diameter, than the inner perimeter 3d of the barrel 3 (FIG. 3B). As such, the polygonal first optical element 1 may be aligned to fit inside the polygonal pocket 3c, while being surrounded by the inner perimeter 3d, despite the circular shape of the inner perimeter 3d. In this respect, it is noted that the inner perimeter 3d refers to a perimeter of a cylinder defined by an inner lateral surface of the barrel 3 that overlaps the spacer 2 and the second optical element 4.

Figure 4A:
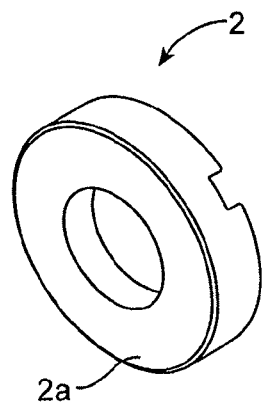
FIG. 4A illustrates an enlarged perspective view of a spacer in FIG. 1A.
Figure 4B:
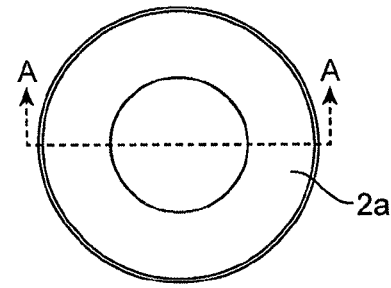
FIG. 4B illustrates a top, plan view of the spacer in FIG. 4A.
Figure 4C:
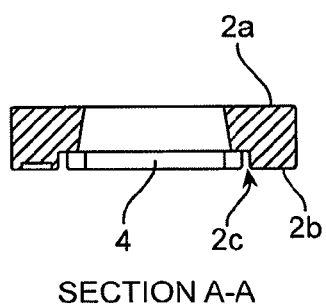
FIG. 4C illustrates a cross-sectional view along line A-A in FIG. 4B.

As illustrated in FIGS. 4A-4B, the spacer 2 has a circular shape with an aperture therethrough, e.g., a toroidal or donut shape. As illustrated in FIG. 4C, the spacer 2 includes an outer surface 2a facing the first optical element 1 when inside the barrel 3 and an inner surface 2b, opposite and parallel to the outer surface 2a, facing the second optical element 4 when inside the barrel 3. The inner surface 2b of the spacer 2 includes a recess defining a polygonal pocket 2c and surrounding the aperture of the spacer 2.

Figure 4D:
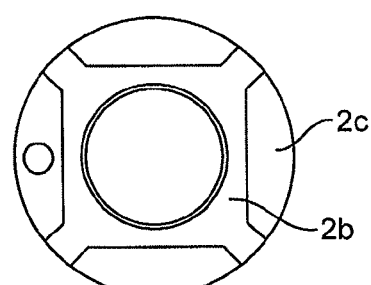
FIG. 4D illustrates a bottom, plan view of the spacer in FIG. 4A.
Figure 6A:
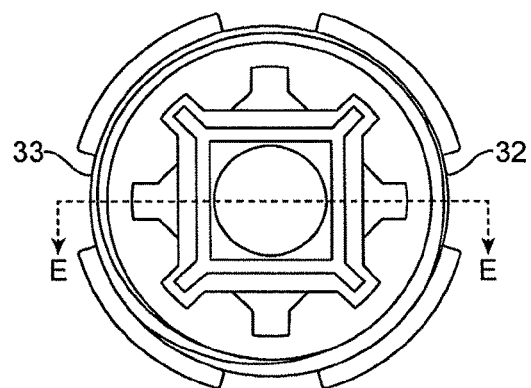
FIG. 6A illustrates a bottom, plan view of a lens barrel according to another embodiment.
Figure 6B:
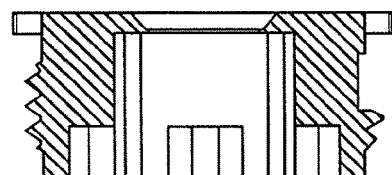
FIG. 6B illustrates a cross-sectional view along line E-E in FIG. 6A.
Figure 6C:
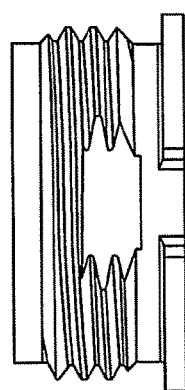
FIG. 6C illustrates a side view of the lens barrel in FIG. 6A.
Figure 6D:
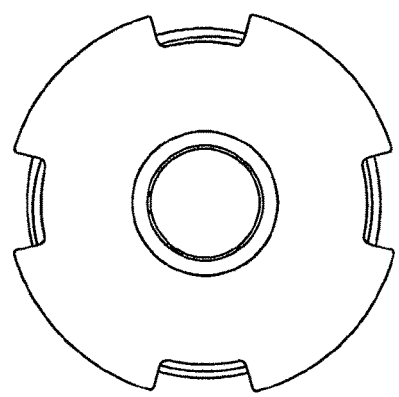
FIG. 6D illustrates a plan view of a front of the lens barrel in FIG. 6A.
Figure 6E:
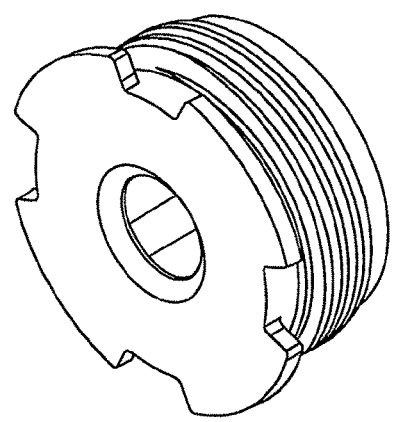
FIG. 6E illustrates a perspective view of the lens barrel in FIG. 6A.

In detail, as illustrated in FIGS. 4C-4D, the inner surface 2b of the spacer 2 has a stepped-structure, e.g., a flat surface and a recess extending from the flat surface to overlap the aperture, to include the polygonal pocket 2c, so a polygonal structure may be accommodated in the polygonal pocket 2c. For example, when viewed from a planar view (FIG. 4D), the polygonal pocket 2c may be a polygonal recess having a depth extending from the inner surface 2b of the spacer 2 toward the outer surface 2a of the spacer 2. For example, referring to FIG. 4C, if a distance along the z-axis between the inner and outer surfaces 2b and 2a of the spacer 2 is a predetermined distance, e.g., about 0.86 mm, a depth of the polygonal pocket 2c may be between a fourth and a third of the predetermined distance, e.g., about 0.25 mm, as measured from the inner surface 2b to the bottom of the polygonal pocket 2c.

The polygonal pocket 2c may correspond in size and shape to the second optical element 4, so at least a portion of the second optical element 2 may be aligned to fit inside the polygonal pocket 2c. For example, as illustrated in FIG. 4C, a thickness of the second optical element 2 may equal the depth of the polygonal pocket 2c, so the entire second optical element 4, e.g., in terms of depth and width, may fit inside the polygonal pocket 2c. The polygonal pocket 2c may also extend from corners thereof, e.g., to allow the second optical element 4 to be flush with the mounting surface in the z-direction, as discussed previously with reference to the extensions in the polygonal pockets 3c of the barrel 3.

For example, when viewed from a planar view (FIG. 4D), the polygonal pocket 2c may have a cross-section having a same shape and size as the polygonal pocket 3c of the barrel 3. For example, the polygonal pocket 2c may be concentric with respect to the inner diameter 3d of the barrel 3, and may have a smaller width, e.g., diameter, than the inner diameter 3d of the barrel 3 (FIG. 2B). As such, the polygonal second optical element 4 may be aligned to fit inside the polygonal pocket 2c despite the circular shapes of the spacer 2 and the inner diameter 3d of the barrel 3. However, the polygonal pockets 3c and 2c may be designed to accommodate other optical elements, e.g., the optical elements may have different widths (FIG. 10A).

According to other embodiments, the polygonal pocket 3c of the barrel 3 may also include alignment marks for aligning the spacer 2 and/or the second optical element 4 within the barrel 3, as discussed with reference to FIGS. 5A-5F and FIGS. 6A-6E.

For example, as can be seen in FIGS. 5A-5F, lenses 1 and 4' may have a same size die, unlike lenses 1 and 4 in FIGS. 1A and 1B. The spacer 2' may simply provide separation between the lenses 1 and 4', i.e., may have no pocket or other registration features. The barrel 3 may include access points 3l, e.g., semi-circular features, adjacent to the polygonal pocket 3c, e.g., surrounding the polygonal pocket 3c, that allows adhesive, e.g., epoxy or glue, to be dispensed to bond the lenses 1, 4 and the spacer 2 to the barrel 3.

In another example, as illustrated in FIGS. 6A-6E, the barrel 3 may include alignment marks 33, e.g., triangular features, adjacent to the polygonal pocket 3c, e.g., surrounding the polygonal pocket 3c, for aligning the second optical element 4. The second optical element 4, i.e., a non-circular element, may be rotated relative to a position of the first optical element, i.e., a non-circular element, into a rotated pocket in the barrel 3. Thus, the spacer 2 is actually integrated in the barrel 3 and the spacing between the first and second optical elements 1 and 4 is controlled by a height of a ledge, e.g., about 0.718 mm, from a bottom rim of the barrel 3. For example, the second optical element 4 may be rotated 45° degrees relative to the first optical element 1 within the barrel 3.

According to other embodiments, an inner diameter of the spacer 2 may be adjusted to minimize stray light from reaching a sensor 9 (FIG. 7C), such as in a camera having an operational waveband, e.g., over any subset of 7.5-13.5 μm or in the visible region. That is, referring to FIGS. 7A-7B, a profile, e.g., a geometric outline, of an inner diameter 2d of the spacer 2 may be curved as illustrated in FIG. 7B, in order to minimize or suppress stray light, thereby improving optical performance. It is noted that stray light includes light that enters an optical system, e.g., a camera, at an angle beyond the field of view, as well as light within the field of view that is reflected within the optical system and scattered. An aperture stop AS at the surface A also helps to restrict the field of view.

Figure 7A:
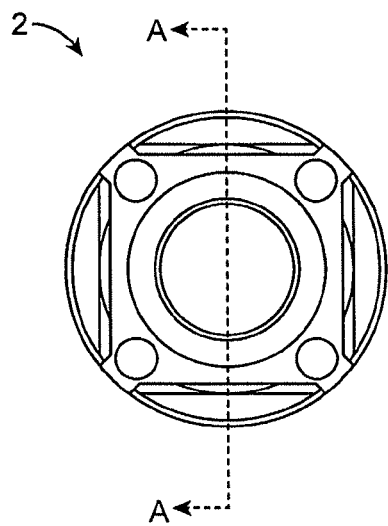
FIG. 7A illustrates a bottom, plan view of a spacer according to another embodiment.
Figure 7B:
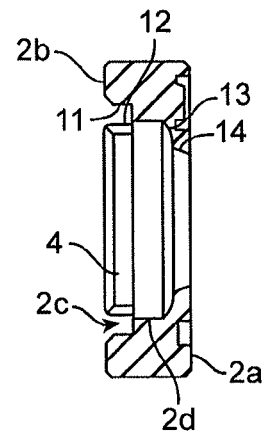
FIG. 7B illustrates a cross-sectional view along line A-A in FIG. 7A.
Figure 7C:
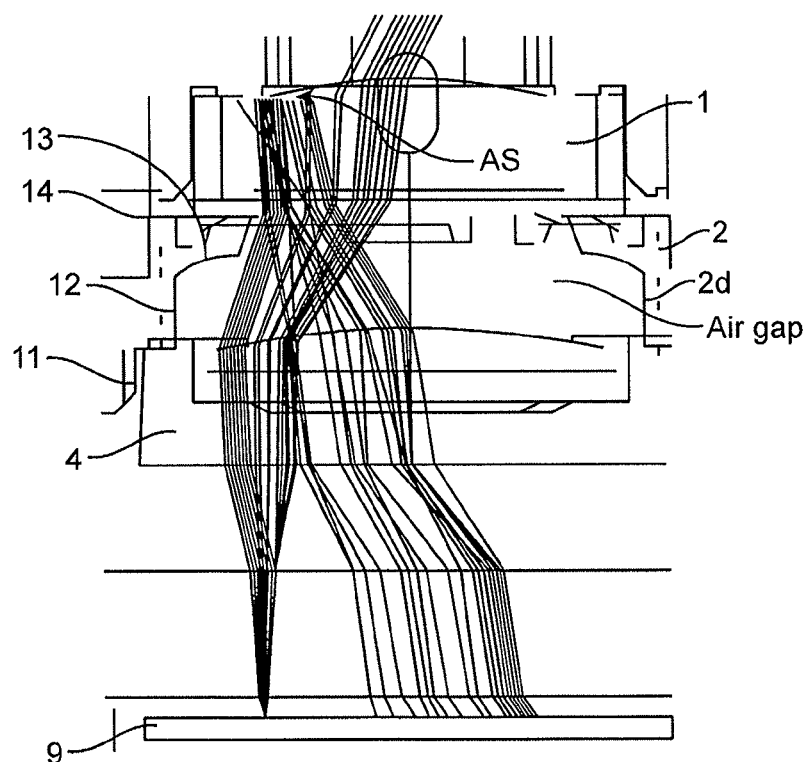
FIG. 7C illustrates a schematic cross-sectional view of a camera including a lens barrel assembly having the spacer in FIG. 7A.

In detail, referring to FIGS. 7B-7C, the inner diameter 2d of the spacer 2, i.e., a surface of the spacer 2 facing the air gap between the first and second optical elements 1 and 4, may include a first portion 11, a second portion 12, a third portion 13, and a fourth portion 14. The first through fourth portions 11 and 14 define a single and continuous surface, and are separately labeled and described for clarity.

As illustrated in FIGS. 7B-7C, the first portion 11 extends from the inner surface 2b of the spacer 2 to define the polygonal pocket 2c, as discussed previously with reference to FIGS. 4C-4D. The second portion 12 extends continuously from the first portion 11, i.e., extends perpendicularly from the polygonal pocket 2c, toward the outer surface 2a of the spacer 2. The third portion 13 curves from the second portion 12 toward the fourth portion 14, e.g., the third portion 13 may be concave with respect to the air gap between the first and second optical elements 1 and 4. The fourth portion 14 connects the third portion to the outer surface 2a and is inclined, e.g., imaginary lines extending and continuing from the fourth portion 14 toward and beyond the outer surface 3a of the barrel 3 define a cone having an angle, i.e., a vertex angle, of about 37 degrees. For example, a thickness of the spacer 2 corresponding to the first portion 11 may be about 0.32 mm, a thickness of the spacer 2 corresponding to the second portion 12 may be about 0.37 mm, the thickness of the spacer 2 corresponding to the third portion 13 may be about 0.11 mm, and a thickness of the spacer 2 corresponding to the fourth portion 14 may be about 0.20 mm, while the thicknesses refer to measurements along a normal to the outer surface 2a.

The profile of the inner diameter 2d of the spacer 2 in FIGS. 7A-7B was derived through an iterative process and optical modeling analyzing optical paths through a barrel assembly. Stray light may be further suppressed by coating an anti-reflective coating on optical elements, e.g., all surfaces in the optical path.

According to other embodiments, an outer diameter of the spacer 2 may be adjusted to include stepped cut-outs. That is, referring to FIGS. 8A-8B, stepped cut-outs in a peripheral portion of the spacer 2 provide a height difference between right-side-up and upside-down orientations of the spacer 2, when the spacer 2 is in a channel of an automated equipment sorter. As such, the automated equipment sorter can sort spacers using only mechanical means, thereby enabling fast and efficient automated sorting.

In other words, according to embodiments, the stepped cut-outs allow a thicker center section of the spacer 2 to fall within a channel of a standard automated part sorter. The difference in height between a right-side-up part sitting within the channel, and an upside-down part riding above the channel, allow the sorter to reject the upside-down part, while passing the properly oriented part, using only mechanical means. In contrast, when the standard automated sorting equipment cannot mechanically discern the difference between a spacer in a right-side-up or upside-down orientations, both equipment cost and cycle time may increase.

Figure 8A:
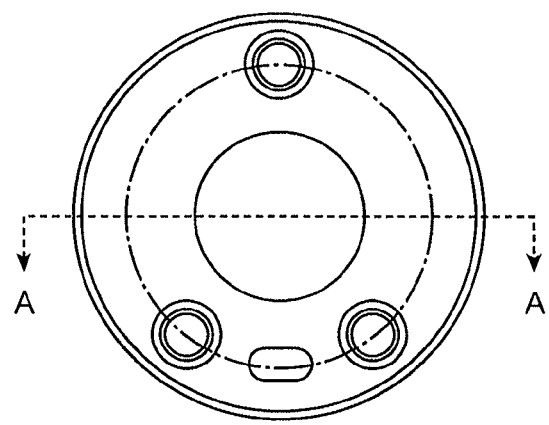
FIG. 8A illustrates a top plan view of a spacer according to another embodiment.
Figure 8B:
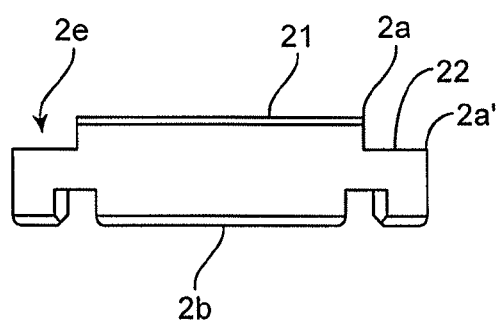
FIG. 8B illustrates a side view of the spacer in FIG. 8A.

In detail, as illustrated in FIG. 8A, side portions of the spacer 2 (cross-hatched) may be removed, so a center portion 2*l* of the spacer 2 extends above side portions 22 of the spacer 2 (FIG. 8B). That is, as illustrated in FIG. 8B, the removed portions define stepped cut-outs 2*e*, i.e., alignment notches 2*e*, from the outer surface 2*a* of the spacer 2, e.g., having a step difference of about 0.30 mm between the outer surface 2*a* and a stepped surface 2*a*'. The center portion 2*l* of the spacer 2 may have a width, e.g., along the x-axis, that is smaller than a width of the channel in the automated sorter equipment, so the center portion 2*l* of the spacer 2 may fit in the channel. Therefore, when the center portion 2*l* fits inside the channel, a distance from a bottom of the channel to the inner surface 2*b* of the spacer is smaller, e.g., as compared to a distance between the bottom of the channel and the outer surface 2*a* when the inner surface 2*b* does not fit in the channel and causes the spacer 2 to be above the channel, indicating improper orientation. As such, the stepped cut-outs 2*e* on the spacer 2 are used to orient the spacer 2 for automated pick-up and placement by the sorting equipment, thereby reducing the complexity and cost of the automated sorters.

According to other embodiments, an outer diameter of the spacer 2 may be adjusted to prevent trapping of gases between the first and second optical elements 1 and 4. That is, referring to FIGS. 9A-9E, a space is defined between an inner diameter of the spacer 2 and an inner diameter 3*d* of the barrel 3, and a notch is formed in a bottom of the spacer 2. Accordingly, trapped gasses may pass from an inner cavity of the spacer 2 outside of the spacer 2 through the defined space and/or through the notch. In contrast, when gasses from the atmosphere are trapped, e.g., during assembly, within the inner cavity of the spacer 2, e.g., between the first and second optical elements 1 and 4, elevated temperatures during the assembly may increase the pressure of the gases, thereby triggering potential distortion or damage to the assembly.

Therefore, according to embodiments, flats 2*g*, e.g., spaces, are formed in an outer diameter 2*f* of the spacer 2 in order to define a gap between the inner cavity of the spacer 2 and the barrel 3 along a width, e.g., an entire width in the xy-plane, of the spacer 2. Notches 2*h* are added in a bottom surface of the spacer 2 to be oriented with the flats 2*g*, thereby allowing passage of trapped gasses from the inner cavity of the spacer 2 outside of the spacer 2. The added flats 2*g* and notches 2*h* prevent gas trapping, i.e., provide venting of gas, while maintaining optical performance. In other words, the flats 2*g* on either side of the spacer 2 define venting channels for an exit path for air that expands during the thermal cure process, e.g., which may potentially cause the optical elements to shift within the barrel 3, while the notches 2*h* are venting features allowing air from the inner cavity of the spacer 2, i.e., from a space between the optical elements 1 and 4, to escape without shifting the optical elements 1 and 4.

Figure 9A:
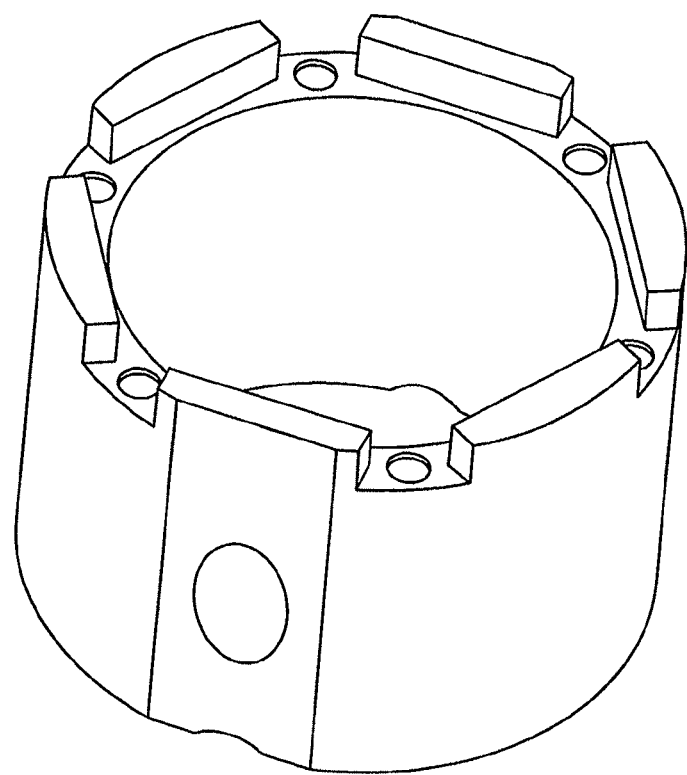
FIG. 9A illustrates a perspective view of a spacer according to another embodiment.
Figure 9B:
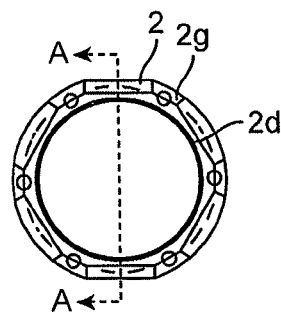
FIG. 9B illustrates a schematic, top plan view of the spacer in FIG. 9A.

In detail, referring to FIG. 9A, a plurality of flats 2*g* may be spaced apart from each other along the outer diameter 2*f* of the spacer 2. As illustrated in FIGS. 9A-9B, each flat 2*g* may extend along a width, e.g., an entire width in a radial direction, of the spacer 2. In other words, each flat 2*g* may be a space between adjacent portions 2*k* of the spacer 2, so the flat 2*g* is in fluid communication with an interior, i.e., an inner cavity 2*s*, of the spacer 2. As a plurality of flats 2*g* is spaced apart from each other and is between the inner diameter 3*d* of the barrel 3 and the inner cavity 2*s* of the spacer 2, a space, e.g., a gap, is defined by each flat 2*g*. Further, as illustrated in FIGS. 9A and 9E, a portion of the spacer 2 is removed, such that a thickness of portion 2*k* of the spacer 2 along a radial direction is smaller than a thickness measured between an inner diameter 2*d* of the spacer 2 and the outer diameter of the spacer 2.

Figure 9C:
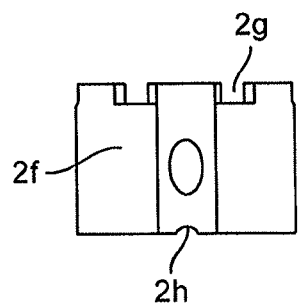
FIG. 9C illustrates a side view of a notch on the spacer of FIG. 9A.
Figure 9D:
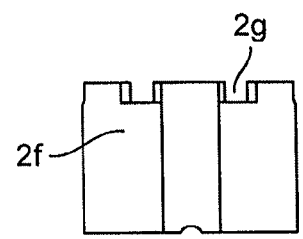
FIG. 9D illustrates another side view of a notch on the spacer of FIG. 9A.
Figure 9E:
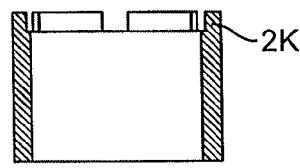
FIG. 9E illustrates a cross-section along line A-A of FIG. 9B.

Further, referring to FIGS. 9A and 9C-9D, the notch 2*h* may be formed in the bottom of the spacer 2, and may extend through an entire thickness of the spacer 2 along the radial direction. That is, the inner cavity 2*s* of the spacer 2 and an exterior of the spacer 2 may be in fluid communication with each other through the notch 2*h*. For example, the notch may have a height of about 0.10 mm and a radius of about 0.40 mm.

According to other embodiments, edge reliefs, e.g., trenches designed into a bottom of a polygonal pocket, are formed to enable a polygonal optical element, e.g., a square-diced lens die, to sit flat within the polygonal pocket, thereby avoiding interference caused when molding interior edges. In contrast, when interior corners of injection molded parts have some rounded parts without edge reliefs, the rounded parts prevent polygonal optical elements, e.g., square lens dies, from sitting flush on their mounting surfaces. For example, when a corner of a polygonal optical element is fitted into a pocket with a rounded inner edge without an edge relief, a sharp edge of the corner of the polygonal optical element cannot mate properly with the rounded surface of the rounded inner edge, i.e., the sharp edge merely has a single point contact with the rounded surface. As such, a gap between the polygonal optical element and the pocket may be defined, thereby causing instability and tilting of the polygonal optical element, thereby degrading optical performance.

Figure 10B:
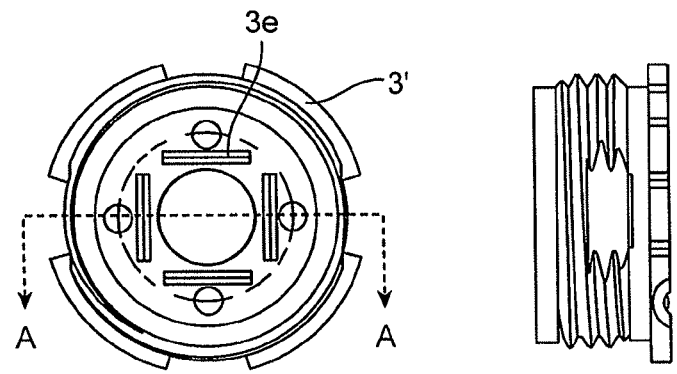
FIG. 10B illustrates a plan bottom view of a disassembled lens barrel of FIG. 10A.
Figure 10C:
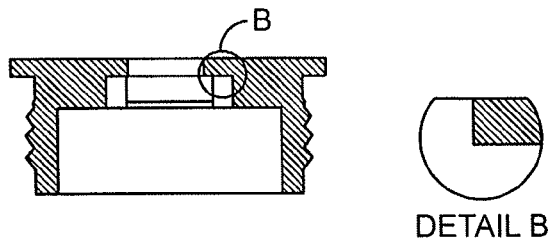
FIG. 10C illustrates a cross-sectional view along line A-A of FIG. 10B.
Figure 10D:
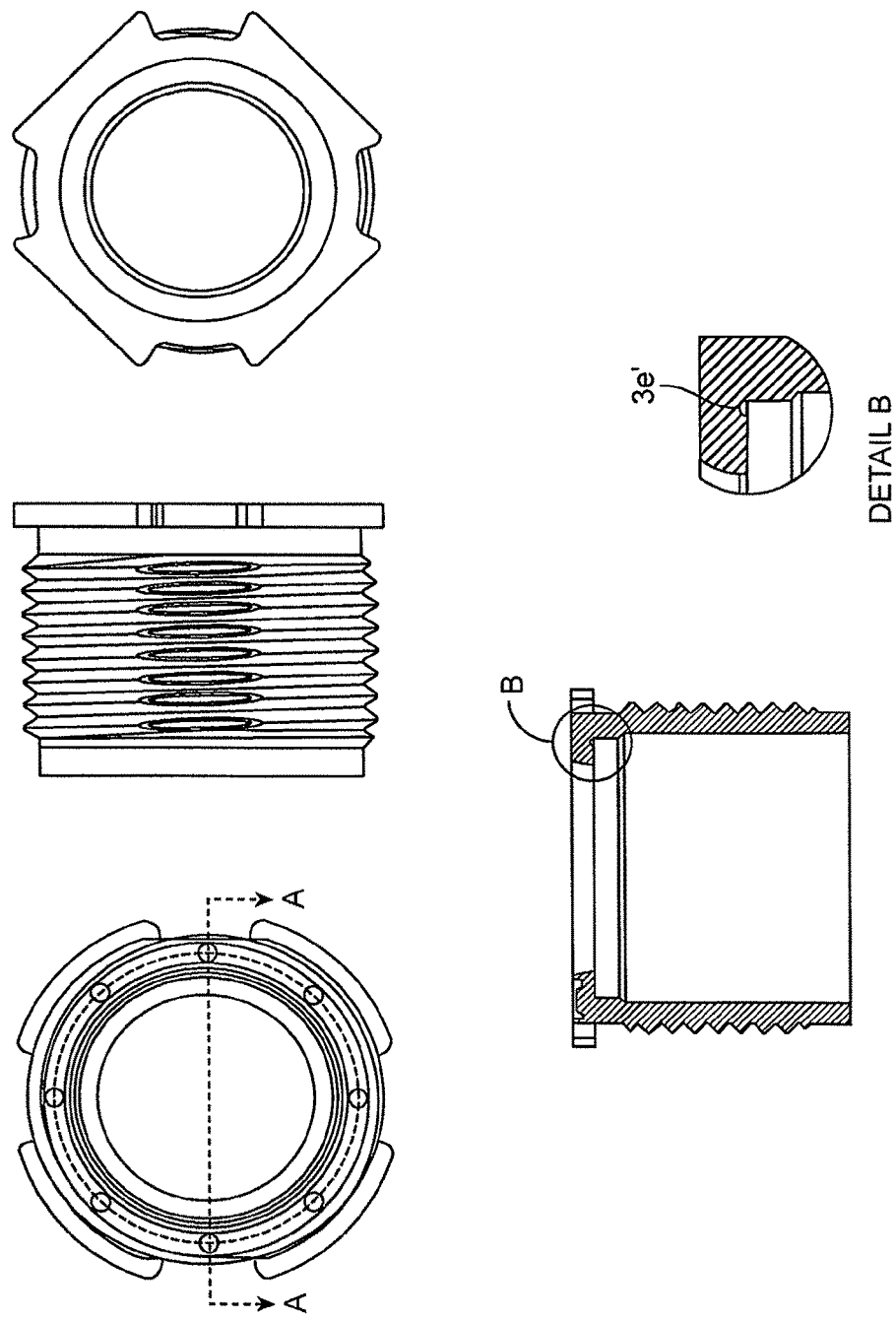
FIG. 10D illustrates a cross-sectional view along line A-A of FIG. 10B according to another embodiment.

Therefore, according to embodiments and as illustrated in FIG. 10A, a barrel 3' may include an edge relief 3*e* in the polygonal pocket 3*c*, so a sharp edge of the first optical element 1 may be properly fitted within the polygonal pocket 3*c*. That is, as illustrated in FIG. 10C (enlarged portions B), the edge relief 3*e* may extend from a corner of the polygonal pocket 3*a* toward the outer surface 3*a*, e.g., as a groove having a polygonal cross-section, so a lateral side of the first optical element 1 may be positioned flush against an inner side surface of the polygonal pocket 3*c*. In another example, as illustrated in FIG. 10D, an edge relief 3*e*' may be a semi-circular groove. For example, a height of the edge relief 3*e* along the z-axis may be about 15% of a height of the polygonal pocket 2*c*, e.g., the height of the edge relief 3*e* may be about 0.050 mm to about 0.085 mm. For example, as further illustrated in plan view of FIG. 10B, each edge relief 3*e* may have a linear shape, so a plurality of edge reliefs 3*e*, e.g., four edge reliefs 3*e*, may be spaced apart from each other and arranged to define a rectangle, e.g., a square.

Figure 11A:
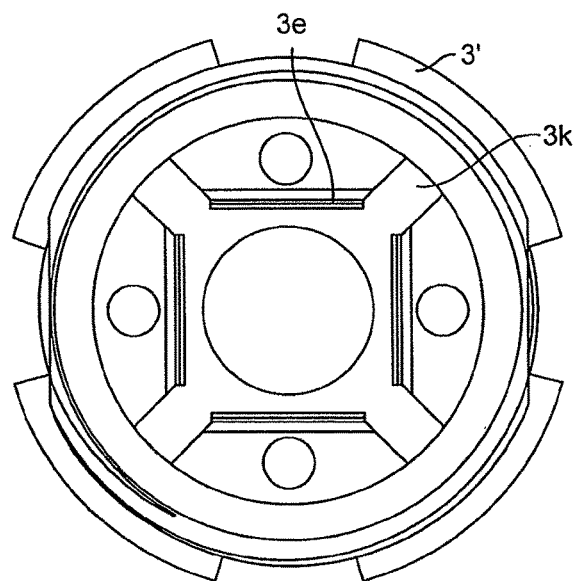
FIG. 11A illustrates an enlarged view of FIG. 10B.
Figure 11B:
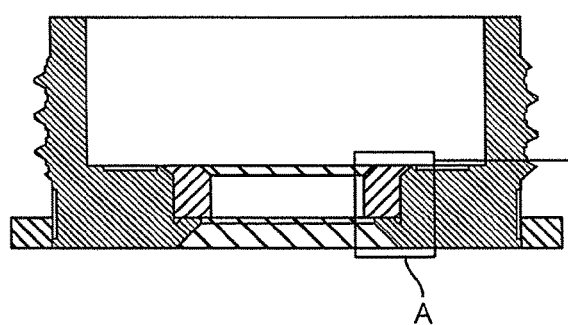
FIG. 11B illustrates a schematic cross section of FIG. 11A.
Figure 11C:
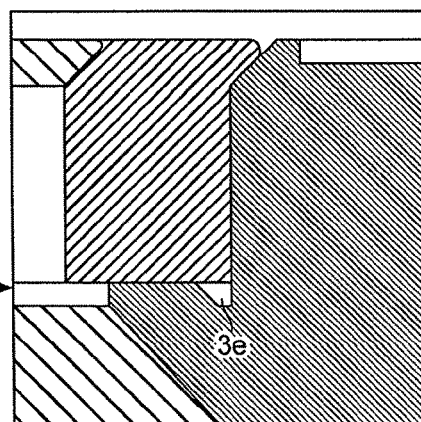
FIG. 11C illustrates an enlarged view of part "A" in FIG. 11B.

In other embodiments, as illustrated in FIGS. 11A-11C, the corner reliefs may be defined by differently shaped protrusions. Further, as discussed previously with reference to the polygonal pocket 3c in FIG. 3A, the extensions of the polygonal pockets 3c may be corner reliefs 3k, as illustrated in FIG. 11A.

Figure 12B:
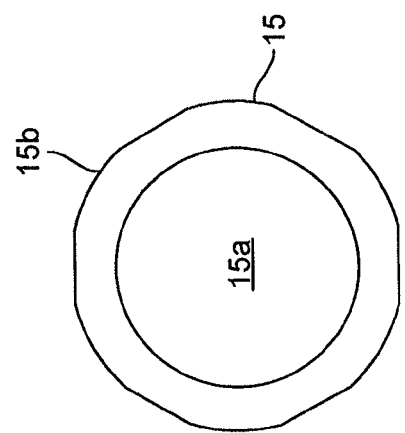
FIGS. 12A and 12B illustrate another cross-section of a non-circular optical element according to another embodiment.
Figure 12A:
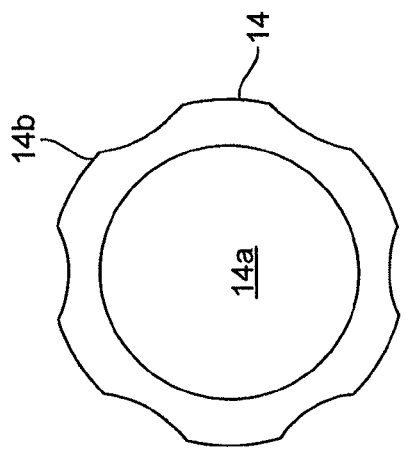
Figure 14:
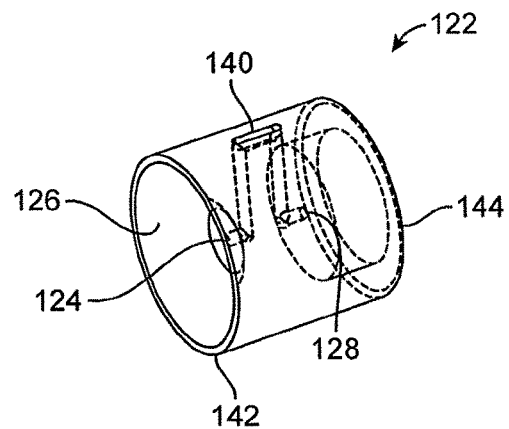
FIG. 14 illustrates a light blocking cartridge with a fluid flow path providing fluid communication between an inlet port and an outlet port.
Figure 15:
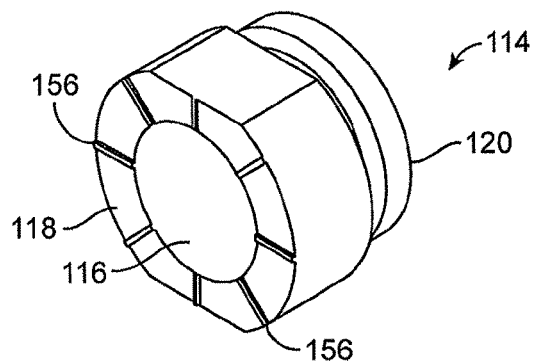
FIG. 15 illustrates a perspective view of a housing or inlet tip configured to receive a light blocking cartridge.
Figure 16:
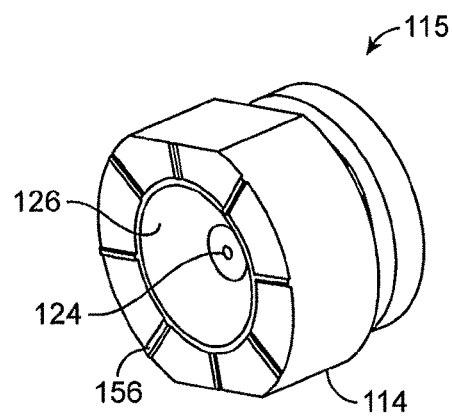
FIG. 16 illustrates a perspective view of a sampling tip with a light blocking cartridge positioned within the bore of the sampling tip.

FIGS. 12A and 12B illustrate other examples of an optical element 14, 15 having a non-circular outer profile or perimeter 14b, 15b with a circular lens 14a, 15a on at least one surface thereof. This particular non-circular cross-section will allow more circular lenses to be packed more tightly on a wafer than an element having a circular profile, while preserving radial symmetry to simplify alignment.

By way of summation and review, according to embodiments, a non-circular die may be aligned and secured in a cylindrical barrel. While the above embodiments are directed to a barrel housing two optical elements, the above embodiment may be adapted to accommodate a single optical element or more than two optical elements. For example, a single optical element may be provided in a pocket in the barrel or may be provided in a space having a pocket. The spacer, the pocket and/or the reliefs may be integral with the barrel itself. Further, the barrel may accommodate a circular element, e.g., a circular die or a circular discretely made optical element. While use of the polygonal dies in a barrel for LWIR imaging may be unconventional, details of the implementation of accommodating these dies, e.g., embodiments directed to a barrel housing two optical elements, corner reliefs, and/or edge reliefs, may be employable in other wavelengths regions in addition to LWIR, e.g., visible.

Method of Making

One or both of optical elements noted above may be silicon. Any one, two, or all of the lens surfaces noted above may be made using, e.g., the stamp and transfer technique disclosed in U.S. Pat. No. 6,027,595, which is hereby incorporated by reference in its entirety. As noted therein, these surfaces may be created on the wafer level, i.e., a plurality of these surfaces may be replicated and transferred to a wafer simultaneously and later singulated to realize individual optical elements. Such singulation may include dicing, core drilling, and/or etching and scribing. Depending on the material of the optical element, other techniques for forming one or more of the lens surfaces may include diamond turning or molding, e.g., high temperature molding.

While the two optical elements discussed above as being silicon, one may be silicon and another may be a more traditional material for LWIR imaging.

Analyte Detector

One or more features of the above optical barrel assembly may be used to aid in blocking light in other optical systems without focusing the light. For example, analyte detectors commonly use sensor assemblies that rely upon a change in light emission, as measured by a light sensor, to indicate the presence of a target analyte. The change in light emission may be a detectible increase or decrease in emitted light. For sensor assemblies measuring an increase or presence of light with dark field detectors, precluding ambient light from entering the light sensor component will improve accuracy and overall sensitivity of the analyte detector.

As described in detail below, one or more embodiments is directed to providing improved light blocking capabilities of a light blocking assembly 115 of housing 112 of analyte detector 110.

With reference to FIGS. 14-20, the fluid flow path 130 from the exterior of the detector 110 to a sensor assembly 154 is defined by the interaction of a sampling tip 114 with a light blocking cartridge 122 inserted in the sampling tip 114. Thus, the cartridge 122 and the sampling tip 114 cooperate to provide the fluid path 130 from the environment to a detector port 152, i.e., the tip 114 and light blocking cartridge 122 provide a light blocking assembly 115. Although depicted in FIG. 13, as the point of entry for samples to be transferred to the sensory assembly 154, the light blocking assembly 115 may be positioned anywhere between an environment and sensor assembly 514. For the purposes of this disclosure, the discussion will describe light blocking assembly 115 as depicted in FIG. 13. When used in other configurations, the ability to block light provided by the cooperation of cartridge 122 with sampling tip 114 will remain the same; however, tip 114 may be simplified to primarily a housing for the cartridge 122.

The sampling tip 114 has a bore 116 passing from a first end 118 to a second end 120. The bore 116 may be cylindrical and serve as a barrel for the light blocking cartridge 122. The bore 116 has an inner diameter corresponding to the outer diameter of the light blocking cartridge 122. Although other configurations for retaining light blocking cartridge 122 within the bore 116 will provide suitable performance for detector 110, a press fit of light blocking cartridge 122 within bore 116 may be used. Thus, friction alone may retain light blocking cartridge 122 within bore 116. To preclude the transmission of light along the mating interface 148 defined by the outer surface of the light blocking cartridge 122 and the inner surface of bore 116, a seal 150, e.g., an O-ring, a gasket or other material suitable for occluding mating interface 148 may be positioned within the bore 116 on the side corresponding to the outlet port 128 of the light blocking cartridge 122. The seal 150 may be formed in place through use of a material such as, but not limited to, room temperature vulcanizing (RTV) sealant, polyurethane, hydrogenated nitrile butadiene rubber (HNBR) and ethylene propylene diene monomer (EPDM). Additionally, inserted gaskets, O-rings or other similar components prepared from the foregoing compounds as well as silicone, fluoro-elastomer rubber, neoprene and polytetrafluoroethylene (PTFE) may be inserted within bore 116 on the outlet port 128 side of light blocking cartridge 122. In general, any composition will suffice for seal 150 provided that the composition does not interfere with the sensor (not shown) in the sensor assembly 154.

The inner diameter of the bore 116 will also be greater than the outer diameter of the detector port 152. Thus, the location of mating interface 148 will be outside of optical space of the detector (not shown) in sensor assembly 154. Additionally, the mating interface 148 will be outside of the fluid flow path defined by the detector port 152. Thus, any ambient light penetrating through mating interface 148 will be precluded by the seal 150 from entering the sensor assembly 154. As depicted in FIG. 13, detector port 152 is a capillary. However, other components may be used to provide fluid communication from light blocking assembly 115 to detector assembly 154. The seal 150 may also provide a fluidic seal and retention of an exit port 152 positioned within the outlet end or second end 120 of tip 114. As depicted in FIG. 13, the port 152 provides fluid communication to the sensor assembly 154.

The configuration of flow path 130 through the light blocking cartridge 122 also contributes to the light blocking capabilities of the light blocking assembly 115. As depicted in FIGS. 14 and 17-22, the flow path 130 has at least two angular transitions. Thus, fluid passing through the light blocking cartridge 122 must change directions at least two times prior to exiting through outlet port 128 and passing into detector port 152. Further, flow path 130 has low dead volume within the fluid pathway. Dead volumes may occur when a flow path intersects a mating interface or when cavities with stagnant or inconsistent flow patterns exist within or adjacent to a fluid flow path. The estimated dead volume surface area (square inch) for the respective flow paths through embodiments in FIGS. 14, 16-20=0.0025 in$^2$. In general, a suitable light blocking assembly 115 has a dead volume ranging from about no dead volume up to 0.0125 square inches, e.g., equal to or less than 0.0075 square inches.

Figure 17:
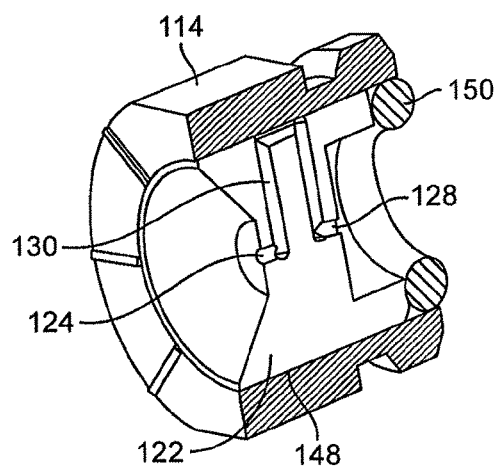
FIG. 17 illustrates a side cut-away perspective view of the device depicted in FIG. 16.
Figure 18:
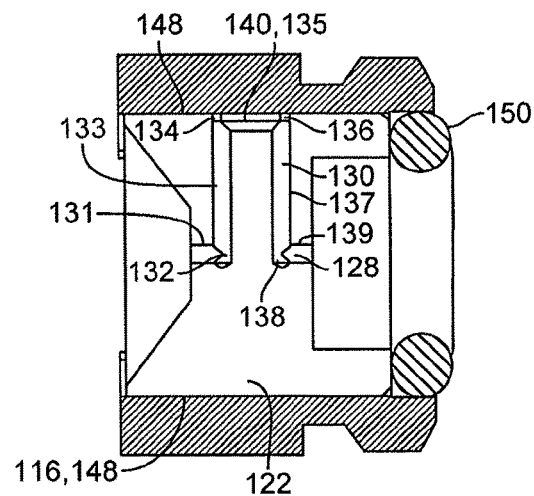
FIG. 18 illustrates a side cut-away view of the device depicted in FIG. 16.

More typically in the embodiments, analyte containing fluid will pass through four angular transitions as depicted in FIGS. 14 and 17-20. With reference to FIGS. 17 and 18, analyte collection area 126 is a recessed area which provides for transfer of analyte from a surface, a swipe, or other collection device into the sampling tip 114 via a pump (not shown) associated with the analyte detector 110. Fluid carrying analyte passes through the inlet port 124 and passes through the fluid path 130 to the outlet port 128. As depicted, the fluid path 130 has five sections 131, 133, 135, 137, 139 defined by angular transitions 132, 134, 136, and 138. In the embodiment of FIGS. 17-20, angular transitions 132, 134, 136 and 138 have minimal dead space, thereby enhancing passage of analyte through the fluid path 130 to the sensor assembly 154.

As depicted in FIGS. 14, 17-20, the flow path section 130 is defined by the inner surface of the bore 116 and a slot 140 in the light blocking cartridge 122. Thus, the configuration of the light blocking cartridge 122 simplifies the manufacturing process by enabling the use of simple drilling techniques to form flow path sections 131, 133, 137, and 139. Thus, one or more embodiments may also reduce overall manufacturing costs. Further, due to the modularity of the tip 114 with the light blocking cartridge 122, one or more embodiments may allow for easy retro-fit of current detectors with the light blocking assembly 115.

Figure 19:
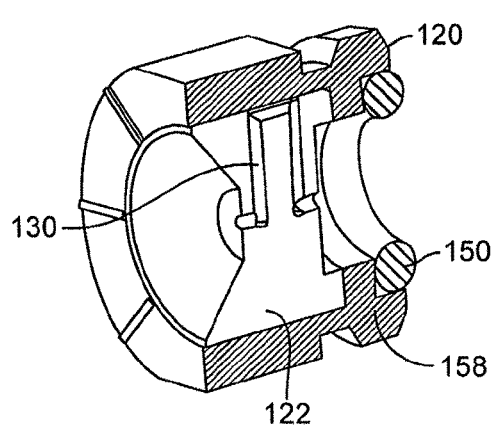
FIG. 19 illustrates a side cut-away perspective view of an alternative embodiment of the device depicted in FIG. 16.
Figure 20:
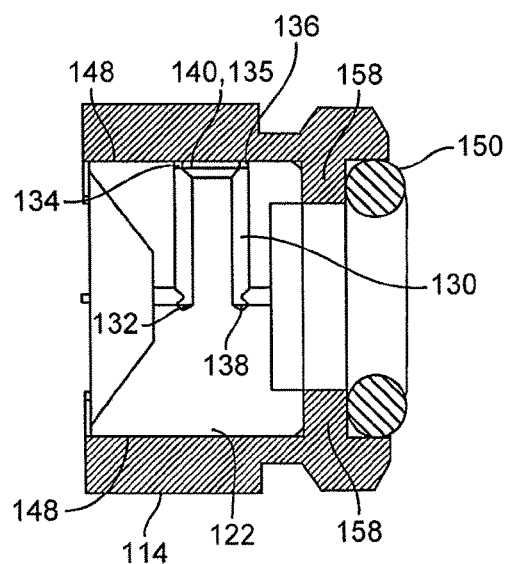
FIG. 20 illustrates a side cut-away view of an alternative embodiment of the device depicted in FIG. 16.

In an alternative embodiment as depicted in FIGS. 19-20, the second end 120 of the tip 114 carries a flange 158 projecting into the interior space of the bore 116. With the light blocking cartridge 122 positioned within the bore 116, the light blocking cartridge 122 may be press fitted within the bore 116 until contacting the flange 158. Thus, the flange 158 will reduce or preclude passage of any light penetrating through the mating interface 148 to the sensor assembly 154. In this embodiment, the seal 150 may provide a fluidic seal and retention of the port 152 positioned within the outlet end or second end 120 of tip 114.

Figure 21:
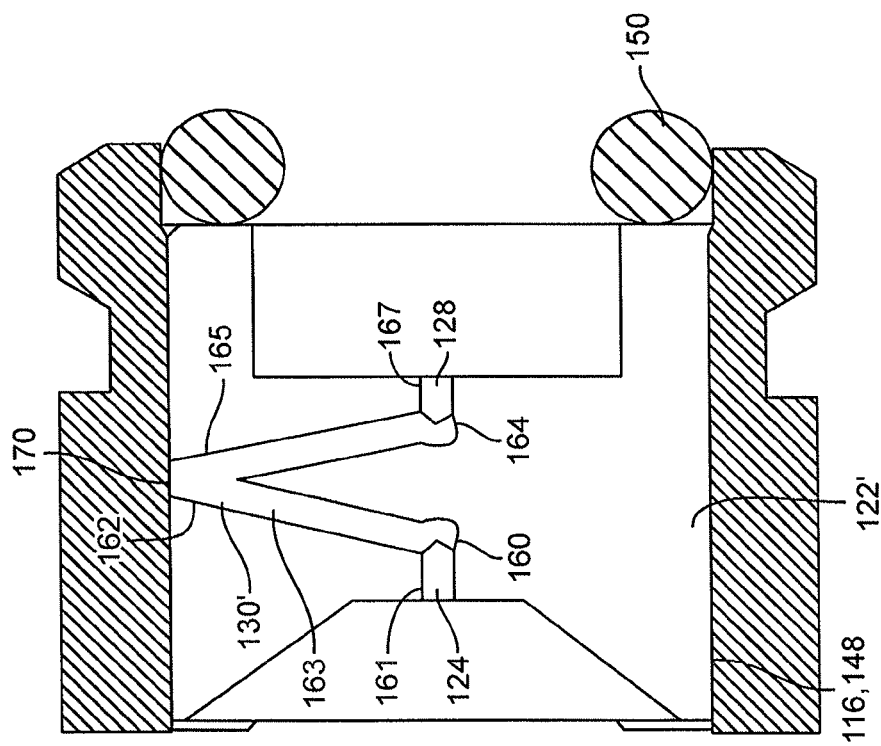
FIG. 21 illustrates a side cut-away view of depicting an alternative embodiment of the light blocking cartridge.

FIG. 21 depicts an alternative embodiment of light blocking cartridge 122'. In this embodiment, the fluid path 130' has three angular transitions 160, 162, and 164 defining flow paths 161, 163, 165, 167. Additionally, the slot 140 has been replaced by a hole 170 having a diameter sufficient to permit drilling of flow paths 163 and 165. As in the embodiment described above, the inner surface of the bore 116 defines a portion of the overall fluid path 130' in the area of the hole 170. Finally, the embodiment of the light blocking cartridge 122' depicted FIG. 9 may be used with either version of the tip 114 depicted in FIGS. 17-20.

Figure 22:
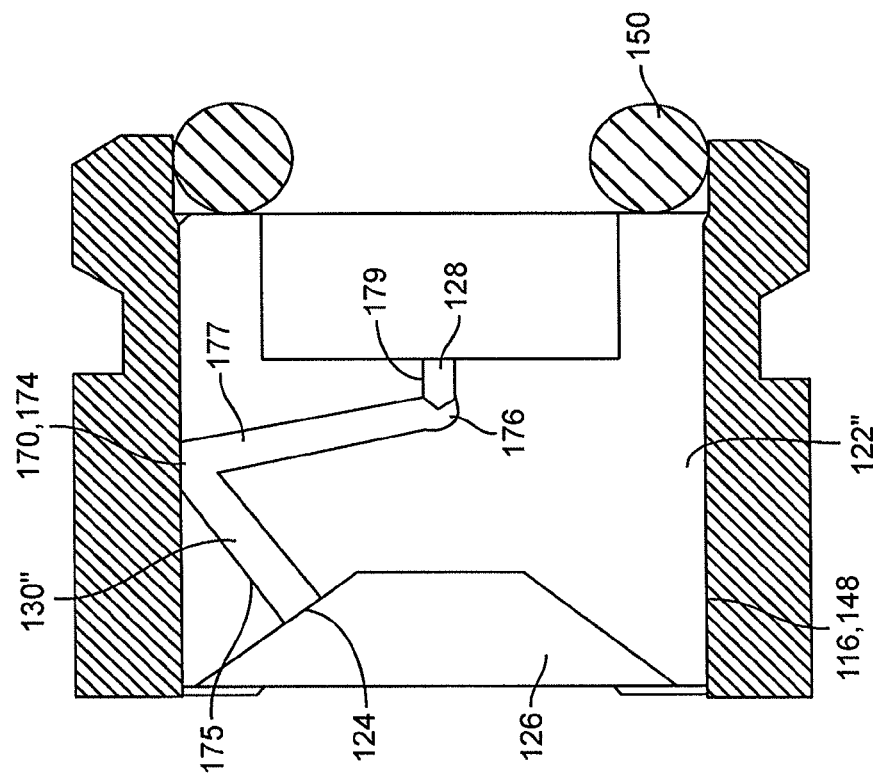
FIG. 22 illustrates a side cut-away view of depicting an alternative embodiment of the light blocking cartridge.

FIG. 22 depicts an alternative embodiment of light blocking cartridge 122". In this embodiment, the fluid path 130" has two angular transitions 174, 176 defining flow paths 175, 177 and 179. The hole 170 has a diameter sufficient to permit drilling of flow paths 175 and 177. As in the embodiment described above, the inner surface of the bore 116 defines a portion of the overall fluid path 130" in the area of the hole 170. Finally, the embodiment of light blocking cartridge 122" depicted FIG. 22 may be used with either version of the tip 114 depicted in FIGS. 17-20.

The angular change relative to the direction of sample flow in any of the flow paths may range from about 10° to about 170°, e.g., from about 20° to about 120°. Further, the range of angular changes may be from about 80° to about 110°. With reference to FIG. 21, the three angular transitions 160, 162, and 164 are 115°, 20°, 115° respectively.

As used herein, the term "and/or" includes any and all combinations of one or more of the associated listed items. Further, although terms such as "first," "second," "third," etc., may be used herein to describe various elements, components, regions, layers and/or sections, these elements, components, regions, layers and/or sections should not be limited by these terms. These terms are only used to distinguish one element, component, region, layer and/or section from another. Thus, a first element, component, region, layer and/or section could be termed a second element, component, region, layer and/or section without departing from the teachings of the embodiments described herein.

Spatially relative terms, such as "beneath," "below," "lower," "above," "upper," etc., may be used herein for ease of description to describe the relationship of one element or feature to another element(s) or feature(s), as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

As used herein, the singular forms is "a," "an" and "the" are intended to include the plural forms as well, unless the context clearly indicates otherwise. It will be further understood that the terms "comprises," "comprising," "includes," and "including" specify the presence of stated features, integers, steps, operations, elements, components, etc., but do not preclude the presence or addition thereto of one or more other features, integers, steps, operations, elements, components, groups, etc.

Embodiments of the present invention have been disclosed herein and, although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the present invention as set forth in the following claims.

What is claimed is:

1. A system comprising:
 a sampling tip housing having a bore defining an inner wall;
 a cartridge disposed within the bore and comprising a fluid path comprising an inlet port configured to receive analyte samples and an outlet port configured to pass the samples to a sensor assembly configured to detect the samples; and a blocking structure configured to obscure a mating surface between the inner wall and the cartridge from the sensor assembly.

2. The system of claim 1, wherein at least a portion of the fluid path is defined by the inner wall and is obscured from the sensor assembly by the blocking structure.

3. The system of claim 1, wherein the fluid path comprises at least two angular transitions within the cartridge.

4. The system of claim 1, wherein the blocking structure comprises an o-ring at least partially disposed within the sampling tip housing.

5. The system of claim 1, wherein the blocking structure comprises a flange integrated with the sampling tip housing and extending into the bore.

6. The system of claim 5, wherein the cartridge is configured to be inserted into the bore and translated to contact the flange.

7. The system of claim 1, wherein the cartridge is configured to be maintained in a press fit engagement with the sampling tip housing while disposed within the bore.

8. The system of claim 1, wherein the cartridge comprises a recess in communication with fluid path and configured to receive a detector port to pass the samples to the sensor assembly.

9. The system of claim 8, wherein the recess comprises a diameter less than a diameter of the light blocking cartridge to offset the detector port from the mating surface.

10. The system of claim 8, further comprising the sensor assembly the detector port, wherein the sampling tip housing, the cartridge, and the blocking structure comprise a light blocking assembly of the system, wherein the inlet port is configured to receive the samples from an environment.

11. A method comprising:
receiving analyte samples at a cartridge disposed within a bore of a sampling tip housing, wherein the bore defines an inner wall, wherein the cartridge comprises a fluid path comprising an inlet port configured to receive the samples;

passing the samples by an outlet port of the fluid path to a sensor assembly configured to detect the samples; and
obscuring a mating surface between the inner wall and the cartridge from the sensor assembly by a blocking structure.

12. The method of claim 11, wherein at least a portion of the fluid path is defined by the inner wall and is obscured from the sensor assembly by the blocking structure.

13. The method of claim 11, wherein the fluid path comprises at least two angular transitions within the cartridge.

14. The method of claim 11, wherein the blocking structure comprises an o-ring at least partially disposed within the sampling tip housing.

15. The method of claim 11, wherein the blocking structure comprises a flange integrated with the sampling tip housing and extending into the bore.

16. The method of claim 15, further comprising:
inserting the cartridge into the bore; and
translating the cartridge within the bore to contact the flange.

17. The method of claim 11, further comprising maintaining the cartridge in a press fit engagement with the sampling tip housing while disposed within the bore.

18. The method of claim 11, wherein the cartridge comprises a recess in communication with fluid path, the method further comprising receiving a detector port in the recess to pass the samples to the sensor assembly.

19. The method of claim 18, wherein the recess comprises a diameter less than a diameter of the light blocking cartridge to offset the detector port from the mating surface.

20. The method of claim 18, wherein the sampling tip housing, the cartridge, and the blocking structure comprise a light blocking assembly, wherein the inlet port is configured to receive the samples from an environment.

* * * * *

UNITED STATES PATENT AND TRADEMARK OFFICE
CERTIFICATE OF CORRECTION

Page 1 of 1

PATENT NO. : 10,288,832 B2
APPLICATION NO. : 15/588411
DATED : May 14, 2019
INVENTOR(S) : Christopher Willis et al.

It is certified that error appears in the above-identified patent and that said Letters Patent is hereby corrected as shown below:

In the Claims

In Column 23, Line 25, change "diameter of the light blocking cartridge" to --diameter of the cartridge--

In Column 23, Line 28, change "assembly the detector port" to --assembly and the detector port--

In Column 24, Lines 31-32, change "diameter of the light blocking cartridge to offset" to --diameter of the cartridge to offset--

Signed and Sealed this
Fourteenth Day of April, 2020

Andrei Iancu
*Director of the United States Patent and Trademark Office*